(12) United States Patent
Park

(10) Patent No.: US 12,219,870 B2
(45) Date of Patent: Feb. 4, 2025

(54) ORGANIC ELECTROLUMINESCENCE DEVICE AND COMPOUND FOR ORGANIC ELECTROLUMINESCENCE DEVICE

(71) Applicant: Samsung Display Co., LTD., Yongin-si (KR)

(72) Inventor: Hye Jeong Park, Hwaseong-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 886 days.

(21) Appl. No.: 17/146,993

(22) Filed: Jan. 12, 2021

(65) Prior Publication Data

US 2021/0359220 A1 Nov. 18, 2021

(30) Foreign Application Priority Data

May 12, 2020 (KR) .................. 10-2020-0056355

(51) Int. Cl.
*H10K 85/60* (2023.01)
*C07D 471/04* (2006.01)
(Continued)

(52) U.S. Cl.
CPC ....... *H10K 85/6572* (2023.02); *C07D 471/04* (2013.01); *H10K 50/15* (2023.02); *H10K 50/16* (2023.02)

(58) Field of Classification Search
CPC .... H10K 85/6572; H10K 50/15; H10K 50/16; C07D 471/04
See application file for complete search history.

(56) References Cited

U.S. PATENT DOCUMENTS 8,475,686 B2 7/2013 Fadhel
9,406,892 B2 8/2016 Zeng et al.
(Continued)

FOREIGN PATENT DOCUMENTS

CN 109180567 A * 1/2019 ........... C07D 213/06
CN 109912593 6/2019
(Continued)

*Primary Examiner* — Christina H. W. Rosebach
(74) *Attorney, Agent, or Firm* — KILE PARK REED & HOUTTEMAN PLLC

(57) ABSTRACT

An organic electroluminescence device includes a first electrode, a second electrode disposed on the first electrode, and functional layers disposed between the first electrode and the second electrode. At least one functional layer of the functional layers includes a compound represented by Formula 1, thereby having low driving voltage, high light emission efficiency, and long life characteristics.

14 Claims, 5 Drawing Sheets

(51) Int. Cl.
*H10K 50/15* (2023.01)
*H10K 50/16* (2023.01)

(56) References Cited

U.S. PATENT DOCUMENTS

| | | |
|---|---|---|
| 9,997,716 B2 | 6/2018 | Zeng et al. |
| 11,258,019 B2 | 2/2022 | Shin et al. |
| 2014/0367656 A1 | 12/2014 | Kim et al. |
| 2017/0179396 A1 | 6/2017 | Kim et al. |
| 2019/0051841 A1 | 2/2019 | Sim et al. |
| 2019/0292169 A1 | 9/2019 | Park et al. |
| 2020/0095224 A1* | 3/2020 | Zhang ............... H10K 85/6572 |

FOREIGN PATENT DOCUMENTS

| | | |
|---|---|---|
| CN | 112724073 | 4/2021 |
| KR | 10-2012-0056418 | 6/2012 |
| KR | 10-2012-0117693 | 10/2012 |
| KR | 10-2015-0136579 | 12/2015 |
| KR | 10-2016-0059336 | 5/2016 |
| KR | 10-2016-0085206 | 7/2016 |
| KR | 10-2017-0075117 | 7/2017 |
| KR | 10-2017-0104718 | 9/2017 |
| KR | 10-2017-0116500 | 10/2017 |
| KR | 10-2017-0127379 | 11/2017 |
| KR | 10-2019-0016638 | 2/2019 |
| KR | 10-2019-0053562 | 5/2019 |
| KR | 10-1984677 | 5/2019 |
| KR | 10-2019-0112243 | 10/2019 |

\* cited by examiner

ORGANIC ELECTROLUMINESCENCE DEVICE AND COMPOUND FOR ORGANIC ELECTROLUMINESCENCE DEVICE

CROSS-REFERENCE TO RELATED APPLICATION(S)

This application claims priority to and benefits of Korean Patent Application No. 10-2020-0056355 under 35 U.S.C. § 119, filed on May 12, 2020 in the Korean Intellectual Property Office, the entire contents of which are incorporated herein by reference.

BACKGROUND

1. Technical Field

The disclosure relates to a compound used in an electron transport region and an organic electroluminescence device including the same.

2. Description of the Related Art

Recently, active development is being conducted for an organic electroluminescence display as an image display apparatus. In contrast to liquid crystal displays and the like, organic electroluminescence displays are so-called self-luminescent display apparatuses in which holes and electrons injected from a first electrode and a second electrode recombine in an emission layer, and thus a luminescent material including an organic compound in the emission layer emits light to implement display.

In the application of an organic electroluminescence device to a display apparatus, there is a continuous demand for an organic electroluminescence device having a low driving voltage, high light emission efficiency, and a long life, and for the development of materials for an organic electroluminescence device that is capable of stably attaining such characteristics.

Development of a material for an electron transport layer, capable of enhancing the characteristics of an organic electroluminescence device by controlling the rate of electron transport and the like is underway.

SUMMARY

The disclosure provides an organic electroluminescence device exhibiting low driving voltage, excellent light emission efficiency, and long life characteristics.

The disclosure also provides a compound for an organic electroluminescence device having low driving voltage, high efficiency, and long life characteristics.

An embodiment of the inventive concept provides a compound represented by Formula 1.

[Formula 1]

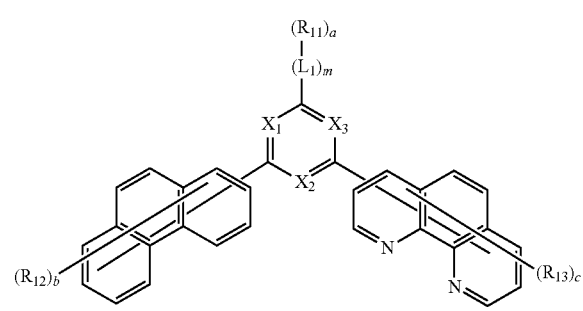

In Formula 1, at least one of $X_1$ to $X_3$ may be N, and the remainder may each be $CR_1$, $R_{11}$ to $R_{13}$ and $R_1$ may each independently be a hydrogen atom, a deuterium atom, a halogen atom, a cyano group, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted aryl group having 6 to 60 ring-forming carbon atoms, or a substituted or unsubstituted heteroaryl group having 1 to 60 ring-forming carbon atoms, $L_1$ may be a direct linkage, a substituted or unsubstituted divalent hydrocarbon ring group having 4 to 60 ring-forming carbon atoms, or a substituted or unsubstituted divalent heterocyclic group having 1 to 60 ring-forming carbon atoms, a may be an integer from 0 to 4, b may be an integer from 0 to 9, c may be an integer from 0 to 7, and m may be an integer from 0 to 3.

In an embodiment, Formula 1 may be represented by Formulas 1-1 to 1-3.

[Formula 1-1]

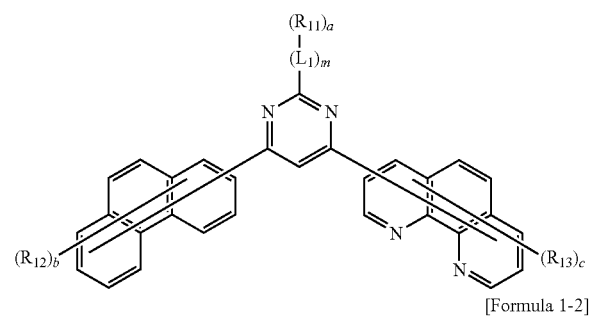

[Formula 1-2]

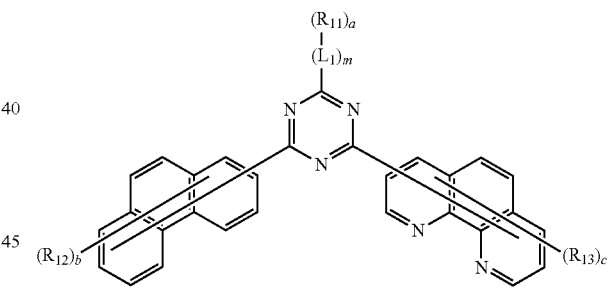

[Formula 1-3]

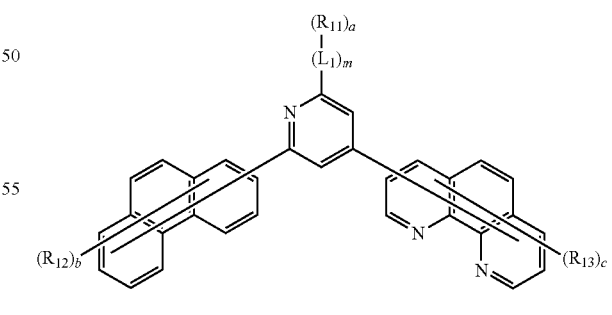

In Formulas 1-1 to 1-3, $R_{11}$, $R_{12}$, $R_{13}$, $L_1$, a to c, and m may be the same as defined in Formula 1.

In an embodiment, Formula 1 may be represented by Formula 1-4 or Formula 1-5.

[Formula 1-4]

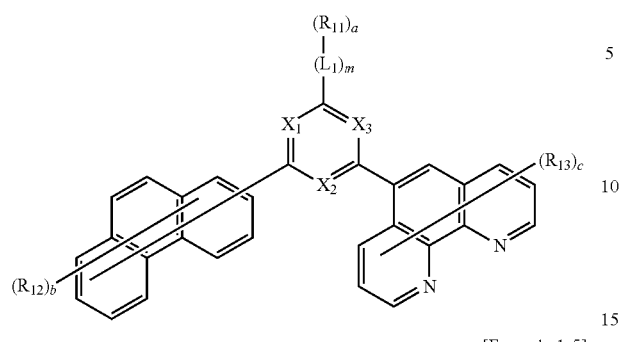

[Formula 1-5]

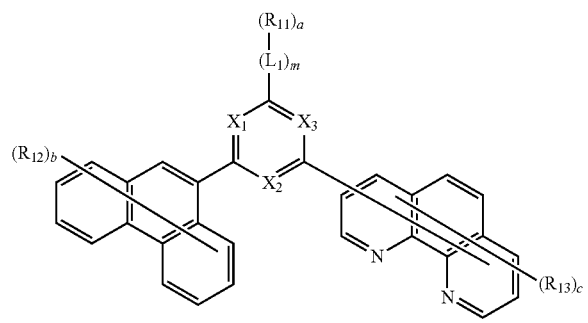

In Formulas 1-4 and 1-5, $R_{11}$, $R_{12}$, $R_{13}$, $L_1$, $X_1$ to $X_3$, a to c, and m may be the same as defined in Formula 1.

In an embodiment, Formula 1 may be represented by Formulas 1A to 1C.

[Formula 1A]

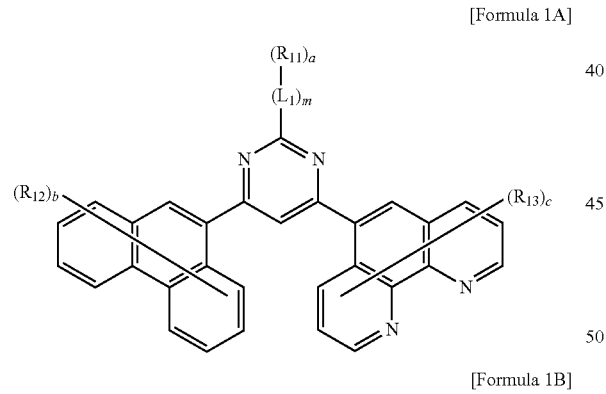

[Formula 1B]

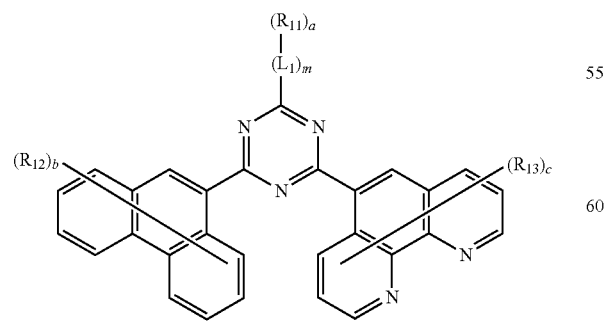

[Formula 1C]

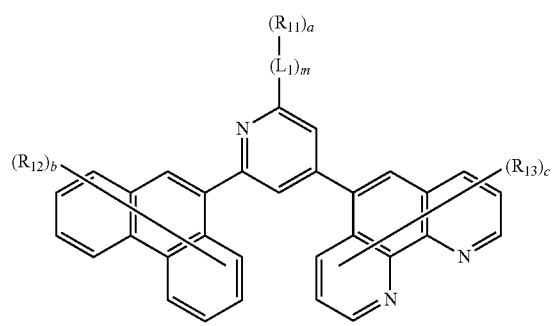

In Formulas 1A to 1C, $R_{11}$, $R_{12}$, $R_1$, $L_1$, a to c, and m may be the same as defined in Formula 1.

In an embodiment, $L_1$ may be a substituted or unsubstituted phenylene group, a substituted or unsubstituted divalent biphenyl group, a substituted or unsubstituted pyridylene group, or a substituted or unsubstituted divalent bipyridyl group.

In an embodiment, $L_1$ may not include a divalent phenanthroline group, and $R_1$ may not include a phenanthroline group.

In an embodiment, $R_{11}$ may be represented by one of Formulas R1-1 to R1-9.

R1-1

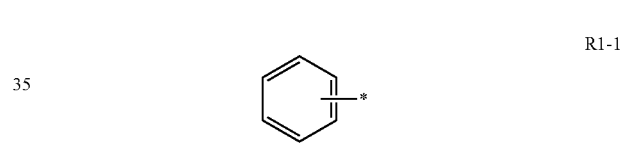

R1-2

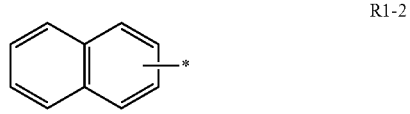

R1-3

R1-4

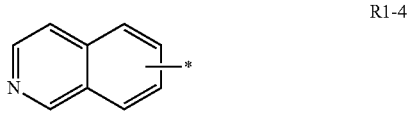

R1-5

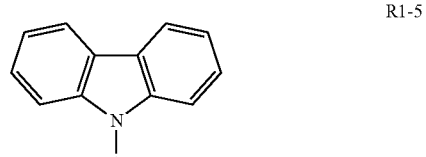

R1-6

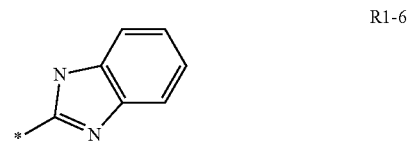

-continued

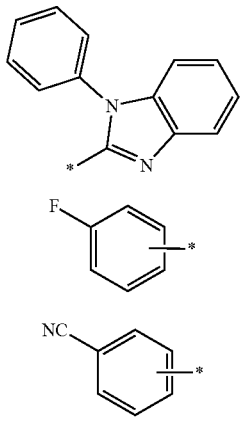

R1-7

R1-8

R1-9

In Formulas R1-1 to R1-9, * indicates a binding site to a neighboring atom.

Another embodiment provides an organic electroluminescence device including a first electrode, a second electrode disposed on the first electrode, and functional layers disposed between the first electrode and the second electrode, wherein at least one of the functional layers includes a compound represented by Formula 1.

In an embodiment, the functional layers may include an emission layer, a hole transport region disposed between the first electrode and the emission layer, and an electron transport region disposed between the emission layer and the second electrode. The electron transport region may include the compound represented by Formula 1.

In an embodiment, the electron transport region may include an electron transport layer, a hole blocking layer disposed between the emission layer and the electron transport layer, and an electron injection layer disposed between the second electrode and the electron transport layer. At least one selected from the electron transport layer, the hole blocking layer, and the electron injection layer may include the compound represented by Formula 1.

In an embodiment, the functional layers may include light emitting units, and at least one charge generating layer disposed between adjacent ones of the light emitting units. At least one selected from the light emitting units and the at least one charge generating layer may include the compound represented by Formula 1.

In an embodiment, each of the light emitting units may include a hole transport region, an emission layer, and an electron transport region which are sequentially stacked, and at least one selected from the electron transport region and the at least one charge generating layer may include the compound represented by Formula 1.

BRIEF DESCRIPTION OF THE DRAWINGS

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION OF THE EMBODIMENTS

Figure 1:
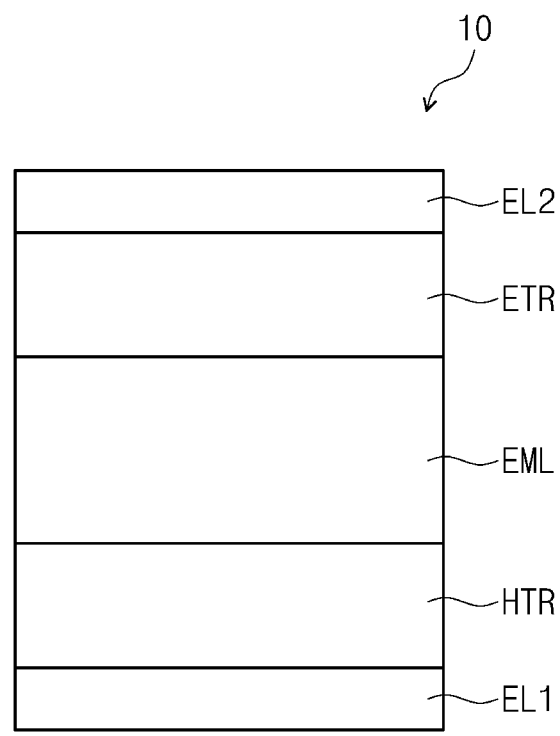
FIG. 1 is a schematic cross-sectional view illustrating an organic electroluminescence device according to an embodiment of the inventive concept.

The inventive concept may be modified in various forms, and thus specific embodiments will be shown in the drawings and described in detail. It should be understood, however, that it is not intended to limit the inventive concept to the embodiments disclosed herein, but rather, is intended to cover all modifications, equivalents, and alternatives included within the spirit and scope of the invention.

In the disclosure, when an element (or a region, a layer, a portion, etc.) is referred to as being "on," "connected to," or "coupled to" another element, it means that the element may be directly disposed on/connected to/coupled to the other element, or that one or more intervening elements may be disposed therebetween.

Like reference numerals refer to like elements throughout the specification. In the drawings, the thickness, the ratio, and the dimensions of elements may be exaggerated for an effective description of technical contents.

The term "and/or," includes all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the inventive concept. The terms of a singular form may include plural forms unless the context clearly indicates otherwise.

Terms such as "below," "lower," "above," "upper," and the like are used to describe the relationship of the configurations shown in the drawings. The terms are used as a relative concept and are described with reference to the direction indicated in the drawings.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within +20%, 10%, or 5% of the stated value.

It should be understood that terms such as "comprises," "comprising," "includes," "including," "have," "having," "contains," and/or "containing" are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

Hereinafter, organic electroluminescence devices according to embodiments of the inventive concept and compounds of embodiments included therein will be described with reference to the accompanying drawings.

FIGS. 1 to 5 are schematic cross-sectional views illustrating organic electroluminescence devices according to embodiments of the inventive concept. Referring to FIGS. 1 to 5, in each of organic electroluminescence devices 10 according to embodiments, a first electrode EL1 and a second electrode EL2 may be disposed to face each other, and functional layers may be disposed between the first electrode EL1 and the second electrode EL2. At least one emission layer EML, EML-1, or EML-2 may be disposed between the first electrode EL1 and the second electrode EL2.

The organic electroluminescence device 10 of embodiments may each further include functional layers between the first electrode EL1 and the second electrode EL2 in addition to emission layers EML. The functional layers may include hole transport regions HTR and electron transport regions ETR.

The organic electroluminescence device 10 according to embodiments may include the first electrode EL1, the hole transport region HTR, the emission layer EML, the electron transport region ETR, and the second electrode EL2 that are sequentially stacked. An organic electroluminescence device 10 of another embodiment may include a capping layer CPL disposed on the second electrode EL2.

In the organic electroluminescence device 10, as voltage is applied to each of the first electrode EL1 and the second electrode EL2, holes injected from the first electrode EL1 move through the hole transport region HTR to the emission layer EML, and electrons injected from the second electrode EL2 move through the electron transport region ETR to the emission layer EML. The electrons and holes recombine in the emission layer EML to form excitons, and these excitons transition from an excited state to a ground state to emit light.

An organic electroluminescence device of an embodiment may include multiple emission layers. The emission layers may be sequentially stacked and provided, and for example, the organic electroluminescence device including the emission layers may emit white light. The organic electroluminescence device including the emission layers may be an organic electroluminescence device having a tandem structure.

Figure 3:
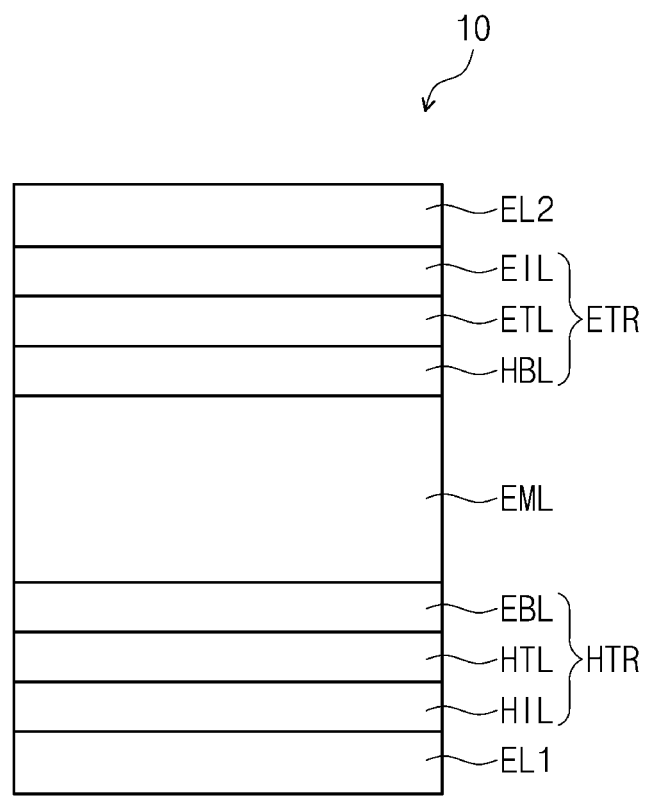
FIG. 3 is a schematic cross-sectional view illustrating an organic electroluminescence device according to an embodiment of the inventive concept.
Figure 4:
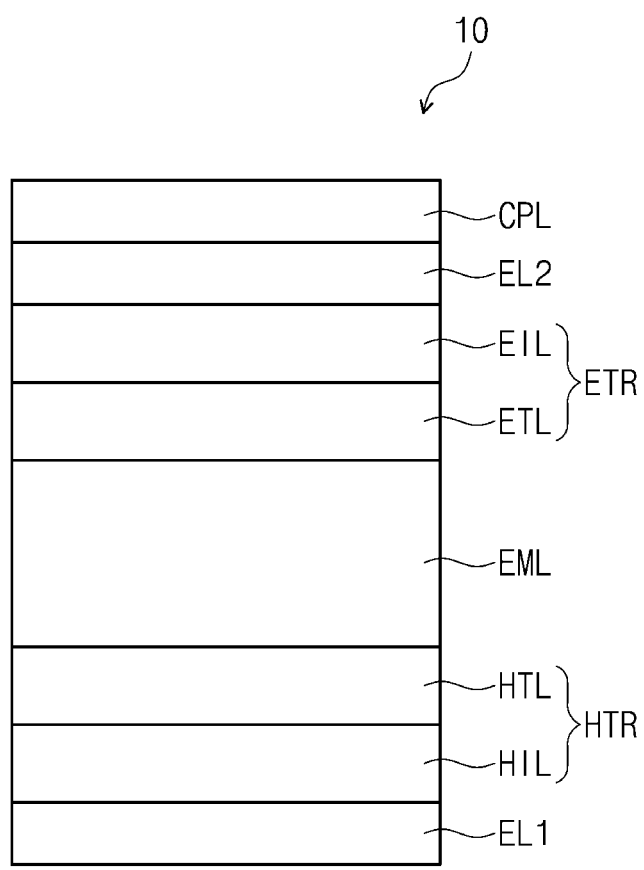
FIG. 4 is a schematic cross-sectional view illustrating an organic electroluminescence device according to an embodiment of the inventive concept.
Figure 5:
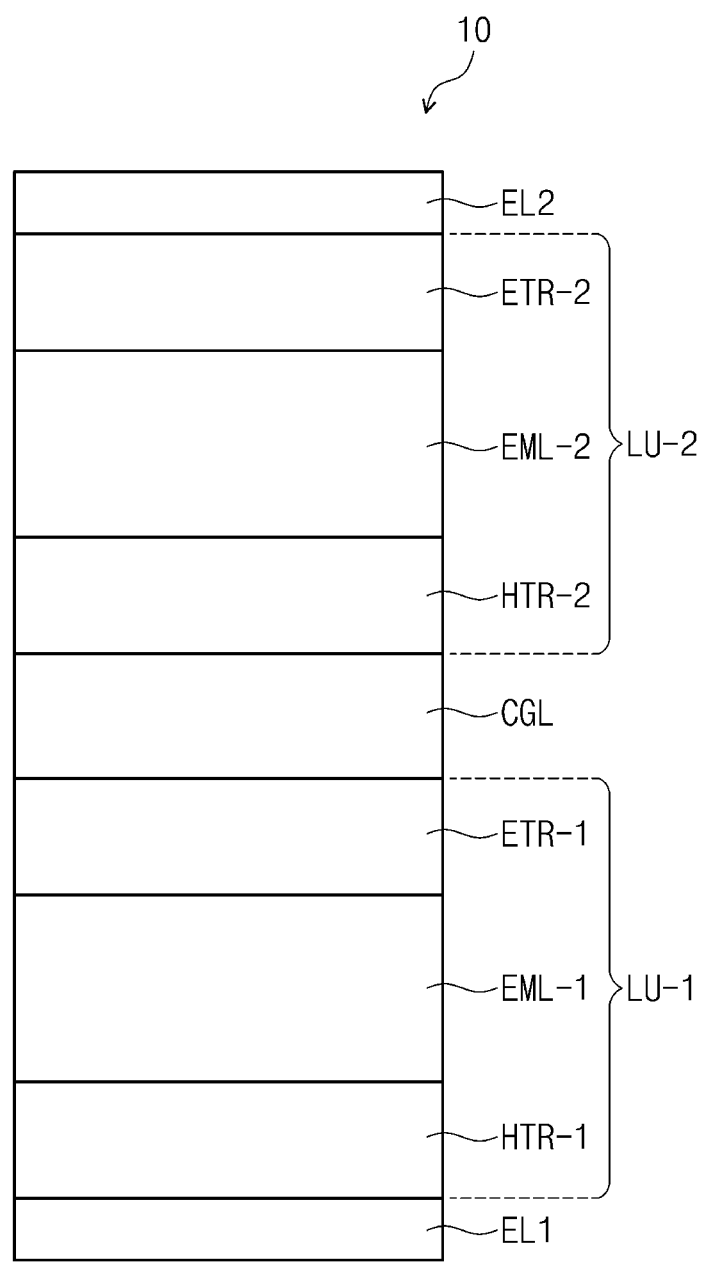
FIG. 5 is a schematic cross-sectional view illustrating an organic electroluminescence device according to an embodiment of the inventive concept.

In FIG. 5, in contrast to FIGS. 1 to 4, an organic electroluminescence device 10 including emission layers EML-1 and EML-2 is illustrated. Referring to FIG. 5, the organic electroluminescence device according to an embodiment may include light emitting units LU-1 and LU-2 containing the emission layers EML-1 and EML-2, respectively.

Figure 2:
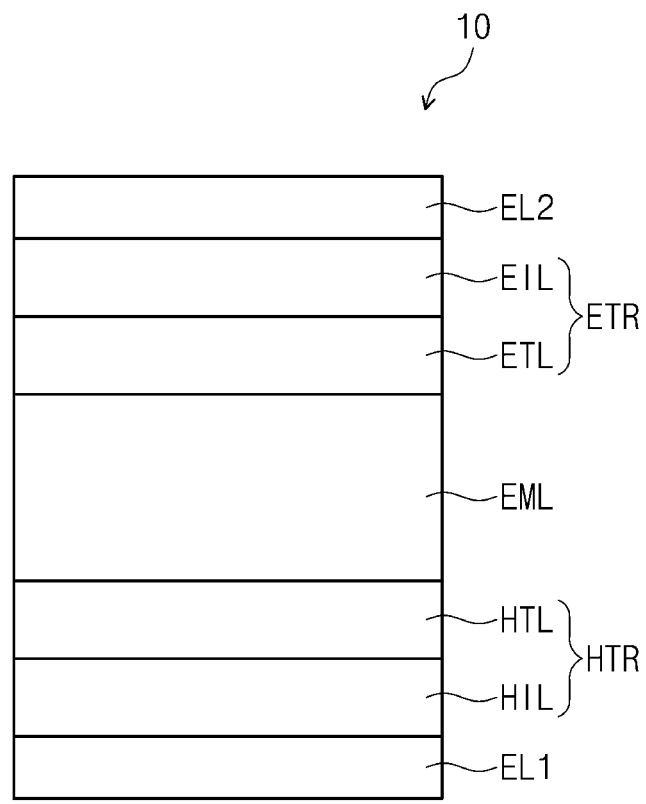
FIG. 2 is a schematic cross-sectional view illustrating an organic electroluminescence device according to an embodiment of the inventive concept.

In comparison to FIG. 1, FIG. 2 shows a schematic cross-sectional view of an organic electroluminescence device 10 of an embodiment, in which a hole transport region HTR includes a hole injection layer IL and a hole transport layer HTL, and an electron transport region ETR includes an electron injection layer EIL and an electron transport layer ETL. In comparison to FIG. 1, FIG. 3 shows a schematic cross-sectional view of an organic electroluminescence device 10 of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 2, FIG. 4 shows a schematic cross-sectional view of an organic electroluminescence device 10 of an embodiment further including a capping layer CPL disposed on the second electrode EL2.

Referring to FIG. 5, the organic electroluminescence device 10 according to an embodiment includes light emitting units LU-1 and LU-2 between the first electrode EL1 and the second electrode EL2. The light emitting units LU-1 and LU-2 include emission layers EML-1 and EML-2, respectively. Each of the light emitting units LU-1 and LU-2 may each respectively include hole transport regions HTR-1 and HTR-2, emission layers EML-1 and EML-2, and electron transport regions ETR-1 and ETR-2 sequentially stacked.

The organic electroluminescence device 10 may include at least one charge generating layer CGL disposed between adjacent ones of light emitting units LU-1 and LU-2. The charge generating layer CGL is a layer capable of generating an electron-hole pair, and holes generated in the charge generating layer CGL may be transferred to one light emitting unit and electrons may be transferred to the other light emitting unit. For example, when the first electrode EL1 is an anode, and the second electrode EL2 is a cathode, electrons generated in the charge generating layer CGL may move to a first light emitting unit LU-1 to form excitons together with holes injected from the first electrode EL1, and the holes may move to a second light emitting unit LU-2 to form excitons together with electrons injected from the second electrode EL2.

The organic electroluminescence device 10 of an embodiment may include a compound of an embodiment, which will be described later, in one of the functional layers disposed between the first electrode EL1 and the second electrode EL2. The organic electroluminescence device 10 of an embodiment may include a compound of an embodiment in electron transport regions ETR, ETR-1, and ETR-2 disposed between the first electrode EL1 and the second electrode EL2. A compound of an embodiment may be included in at least one of the electron injection layer EIL, the electron transport layer ETL, and the hole blocking layer HBL included in the electron transport region ETR. In an embodiment where the organic electroluminescence device 10 includes light emitting units LU-1 and LU-2 as illustrated in FIG. 5, a compound of an embodiment may be included in at least one selected from the electron transport regions ETR-1 and ETR-2 and the at least one charge generating layer CGL.

The compound of an embodiment may be represented by Formula 1.

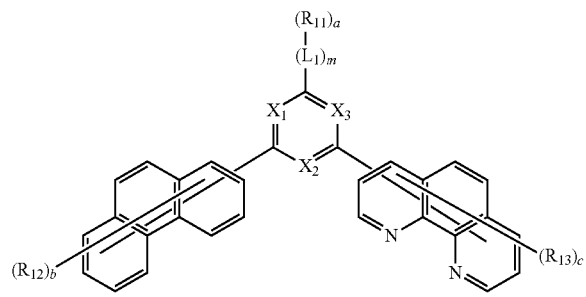

[Formula 1]

The first electrode EL1 has conductivity. The first electrode EL1 may be formed of a metal alloy or a conductive compound. The first electrode EL1 may be an anode. However, embodiments of the inventive concept are not limited thereto, and the first electrode EL1 may be a cathode. The first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide such as indium tin oxide (ITO), indium zinc oxide (IZO), zinc oxide (ZnO), and indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). For example, the first electrode EL1 may have a multilayer structure including a reflective film or a transflective film formed of the above-described materials, and a transparent conductive film formed of indium tin oxide (ITO), indium zinc oxide (IZO), zinc oxide (ZnO), indium tin zinc oxide (ITZO), etc. For example, the first electrode EL1 may have a three-layer structure of ITO/Ag/ITO, but is not limited thereto. The thickness of the first electrode EL1 may be in a range of about 700 Å to about 10,000 Å. For example, the thickness of the first electrode EL1 may be in a range of about 700 Å to about 3,000 Å.

The second electrode EL2 may be disposed to face the first electrode EL1 and include at least one emission layer EML, EML-1, or EML-2 between the first electrode EL1 and the second electrode EL2. The second electrode EL2 may be provided on the electron transport region ETR. The second electrode EL2 may be a common electrode. The second electrode EL2 may be a cathode or an anode. When the first electrode EL1 is an anode, the second electrode EL2 may be a cathode, and when the first electrode EL1 is a cathode, the second electrode EL2 may be an anode. The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, a compound thereof, or a mixture thereof (e.g., AgMg, AgYb, or MgAg). For example, the second electrode EL2 may have a multilayer structure including a reflective film or a transflective film formed of the above-described materials, and a transparent conductive film formed of indium tin oxide (ITO), indium zinc oxide (IZO), zinc oxide (ZnO), indium tin zinc oxide (ITZO), etc.

Although not shown, the second electrode EL2 may be connected with an auxiliary electrode. When the second electrode EL2 is connected with the auxiliary electrode, the resistance of the second electrode EL2 may decrease.

In the organic electroluminescence devices 10 of embodiments illustrated in FIGS. 1 to 5, the electron transport regions ETR, ETR-1, and ETR-2 are provided on the emission layers EML, EML-1, and EML-2. The electron transport region ETR may be provided between the second electrode EL2 and the emission layer EML. The electron transport region ETR may include at least one of the hole blocking layer HBL, the electron transport layer ETL, and the electron injection layer EIL, but embodiments of the inventive concept are not limited thereto.

The electron transport region ETR may have a single layer formed of a single material, a single layer formed of different materials, or a multilayer structure including layers formed of different materials.

For example, the electron transport region ETR may have a single layer structure of an electron injection layer EIL or an electron transport layer ETL, and may have a single layer structure formed of an electron injection material and an electron transport material. For example, the electron transport region ETR may have a single layer structure formed of different materials, or may have a structure in which an electron transport layer ETL/electron injection layer EIL or a hole blocking layer HBL/electron transport layer ETL/electron injection layer EIL are stacked in order from the emission layer EML, but is not limited thereto. The thickness of the electron transport region ETR may be, for example, in a range of about 300 Å to about 1,500 Å.

The electron transport region ETR may be formed using various methods such as a vacuum deposition method, a spin coating method, a cast method, a Langmuir-Blodgett (LB) method, an inkjet printing method, a laser printing method, a laser induced thermal imaging (LITI) method, etc.

In the organic electroluminescence device 10 of an embodiment, the electron transport regions ETR, ETR-1, and ETR-2 may include a compound represented by Formula 1.

In the description, the term "substituted or unsubstituted" may indicate that one is substituted or unsubstituted with at least one substituent selected from the group consisting of a deuterium atom, a halogen atom, a cyano group, a nitro group, an amine group, a silyl group, oxy group, thio group, sulfinyl group, sulfonyl group, carbonyl group, a boron group, a phosphine oxide group, a phosphine sulfide group, an alkyl group, an alkenyl group, an alkoxy group, a hydrocarbon ring group, an aryl group, and a heterocyclic group. Each of the substituents described above may be substituted or unsubstituted. For example, a biphenyl group may be interpreted as an aryl group or as a phenyl group substituted with a phenyl group.

In the description, examples of a halogen atom may include a fluorine atom, a chlorine atom, a bromine atom, and an iodine atom.

In the description, an alkyl group may be a linear, branched, or cyclic type. The number of carbon atoms in the alkyl group is 1 to 50, 1 to 30, 1 to 20, 1 to 10, or 1 to 6.

Examples of the alkyl group may include a methyl group, an ethyl group, an n-propyl group, an isopropyl group, an n-butyl group, a s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but are not limited thereto.

In the description, an aryl group means any functional groups or substituents derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but are not limited thereto.

In the description, a fluorenyl group may be substituted, and two substituents may be bonded to each other to form a spiro structure. An example that the fluorenyl group is substituted is as follows. However, embodiments of the inventive concept are not limited thereto.

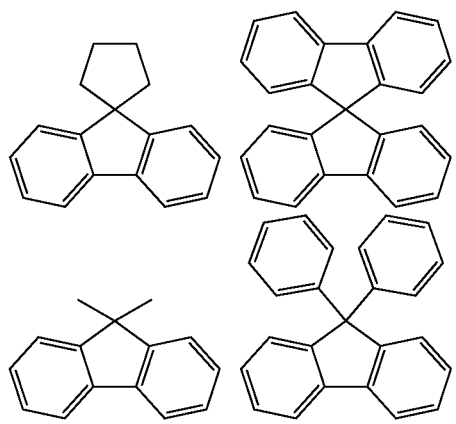

In the description, a heterocyclic group means any functional groups or substituents derived from a ring containing at least one of B, O, N, P, Si, or S as a hetero atom. The heterocyclic group includes an aliphatic heterocyclic group and an aromatic heterocyclic group. The aromatic heterocyclic group may be a heteroaryl group. The aliphatic heterocycle and aromatic heterocycle may be monocyclic or polycyclic.

In the description, heterocycle may include at least one of B, O, N, P, Si or S as a hetero atom. When the heterocycle contains two or more hetero atoms, the two or more hetero atoms may be the same as or different from each other. The heterocycle may be a monocyclic heterocycle or a polycyclic heterocycle, and include heteroaryl. The number of ring-forming carbon atoms in the heterocycle may be 2 to 30, 2 to 20, or 2 to 10.

In the description, an aliphatic heterocyclic group may include at least one of B, O, N, P, Si, or S as a hetero atom. The number of ring-forming carbon atoms in the aliphatic heterocyclic group may be 2 to 30, 2 to 20, or 2 to 10. Examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but are not limited to thereto.

In the description, a heteroaryl group may include at least one of B, O, N, P, Si, or S as a hetero atom. When the heteroaryl group contains two or more hetero atoms, the two or more hetero atoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but are not limited thereto.

In the description, a direct linkage may refer to a single bond.

In the description, "—" indicates a binding site to a neighboring atom.

A compound of an embodiment may be represented by Formula 1.

[Formula 1]

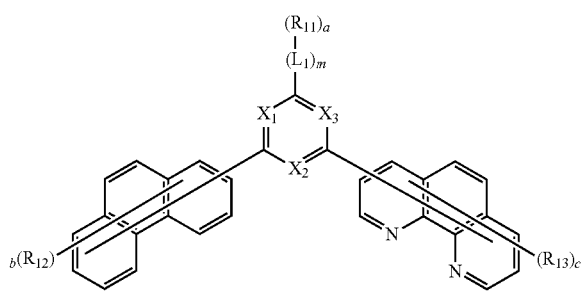

In Formula 1, at least one of $X_1$ to $X_3$ may be N, and the remainder may each be $CR_1$. For example, a ring group containing $X_1$ to $X_3$ may include at least one nitrogen atom. The ring group of the compound of an embodiment may be one of a pyridine having one N, a pyrimidine having two N's, and a triazine having three N's. The compound of an embodiment may be a compound in which a carbon atom of a ring group having at least one N is bonded to phenanthroline or phenanthrene.

In the compound of an embodiment represented by Formula 1, $L_1$ may be a direct linkage, a substituted or unsubstituted divalent hydrocarbon ring group having 4 to 60 ring-forming carbon atoms, or a substituted or unsubstituted divalent heterocyclic group having 1 to 60 ring-forming carbon atoms.

In the compound of an embodiment, $L_1$ may be a direct linkage, a substituted or unsubstituted arylene group having 6 to 60 ring-forming carbon atoms, or a substituted or unsubstituted heteroarylene group having 1 to 60 ring-forming carbon atoms.

For example, in the compound of an embodiment, $L_1$ may be a substituted or unsubstituted phenylene group, a substituted or unsubstituted divalent biphenyl group, a substituted or unsubstituted pyridylene group, or a substituted or unsubstituted divalent bipyridyl group. However, embodiments of the inventive concept are not limited thereto.

In the compound of an embodiment, $L_1$ may not include a divalent phenanthroline group, and $R_1$ may not include a phenanthroline group.

In Formula 1, m may be an integer from 0 to 3. When m is 2 or more, groups represented by $L_1$ may be the same as or different from each other. For example, when m is 2, groups represented by $L_1$ may be different from each other as a perylene group and a pyridylene group, respectively.

In the compound of an embodiment represented by Formula 1, $R_{11}$ may be bonded to $L_1$. When m is 0, $R_{11}$ may be directly bonded to a ring group including $X_1$ to $X_3$. $R_{12}$ may be bonded to a phenanthrene group bonded to a ring group including $X_1$ to $X_3$. $R_{13}$ may be bonded to a phenanthroline group bonded to a ring group including $X_1$ to $X_3$.

In the compound of an embodiment represented by Formula 1, $R_n$ to $R_{13}$, and $R_1$ may each independently be a hydrogen atom, a deuterium atom, a halogen atom, a cyano group, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted aryl group having 6 to 60 ring-forming carbon atoms, or a substituted or unsubstituted heteroaryl group having 1 to 60 ring-forming carbon atoms.

In Formula 1, a may be an integer from 0 to 4. When a is 2 or more, groups represented by $R_{11}$ may be the same as or different from each other. In Formula 1, b may be an integer from 0 to 9. When b is 2 or more, groups represented by $R_{12}$ may be the same as or different from each other. In Formula 1, c may be an integer from 0 to 7. When c is 2 or more, groups represented by $R_{13}$ may be the same as or different from each other.

In the compound of an embodiment represented by Formula 1, $R_{11}$, $R_{12}$, and $R_{13}$ may each independently be a hydrogen atom or a deuterium atom. However, embodiments of the inventive concept are not limited thereto.

In the compound of an embodiment, Ru may be represented by one of Formulas R1-1 to R1-9.

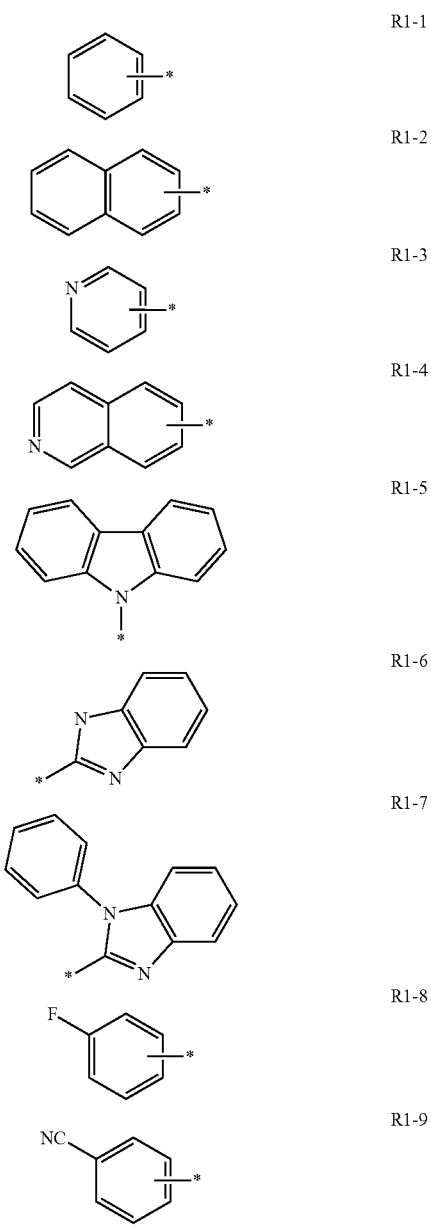

In Formulas R1-1 to R1-9, * indicates a binding site to a neighboring atom.

The compound of an embodiment represented by Formula 1 may be a compound including one divalent phenanthroline group bonded to a ring group containing $X_1$ to $X_3$ in Formula 1. Driving voltage, efficiency, and lifespan characteristics of an organic electroluminescence device including the compound of an embodiment may be controlled by adjusting the number of bonded phenanthroline groups. However, embodiments of the inventive concept are not limited thereto.

The compound of an embodiment represented by Formula 1 may be represented by one of Formulas 1-1 to 1-5.

[Formula 1-1]

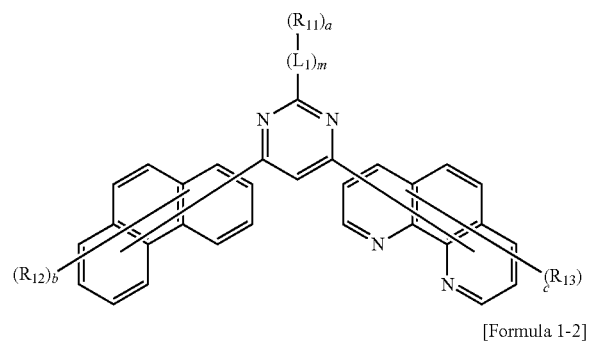

[Formula 1-2]

[Formula 1-3]

[Formula 1-4]

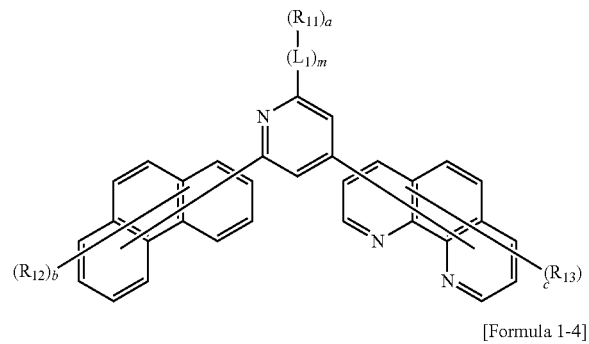

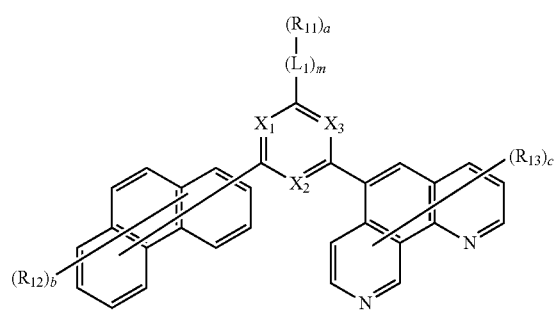

[Formula 1-5]

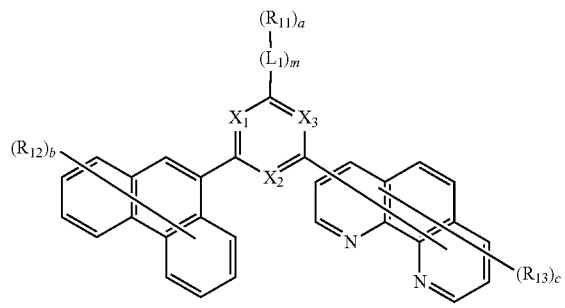

Formula 1-1 is an embodiment where the compound represented by Formula 1 includes a pyrimidine ring group, and Formula 1-2 is an embodiment where the compound represented by Formula 1 includes a triazine ring group. Formula 1-3 is an embodiment where the compound represented by Formula 1 includes a pyridine ring group. The compound of an embodiment includes a ring group containing a nitrogen atom having less electrons than a benzene ring group, and may thus have a better electron transport ability.

The bonding positions of phenanthrene and phenanthroline included in the compound of an embodiment may be as shown below.

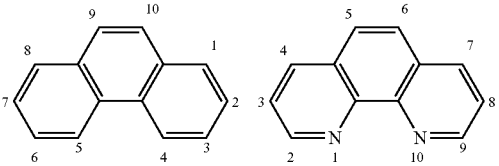

Formula 1-4 specifies a bonding position of a phenanthroline group bonded to a ring group containing $X_1$ to $X_3$. The compound of an embodiment that may be represented by Formula 1-4 may include a structure in which the ring group containing $X_1$ to $X_3$ is bonded at position 5 or position 6 when phenanthroline is 1,10-phenanthroline.

In the compound of an embodiment, Formula 1-5 specifies a bonding position of a phenanthrene group bonded to a ring group containing $X_1$ to $X_3$. The compound of an embodiment that may be represented by Formula 1-5 may include a structure in which the ring group containing $X_1$ to $X_3$ is bonded at position 9 or position 10 of phenanthrene.

In Formulas 1-1 to 1-3 above, $R_{11}$, $R_{12}$, $R_{13}$, $L_1$, a to c, and m may be the same as defined in Formula 1. In Formulas 1-4 and 1-5 above, $R_{11}$, $R_{12}$, $R_{13}$, $L_1$, $X_1$ to $X_3$, a to c, and m may be the same as defined in Formula 1.

The compound of an embodiment represented by Formula 1 may be represented by Formulas 1A to 1C.

[Formula 1A]

[Formula 1B]

[Formula 1C]

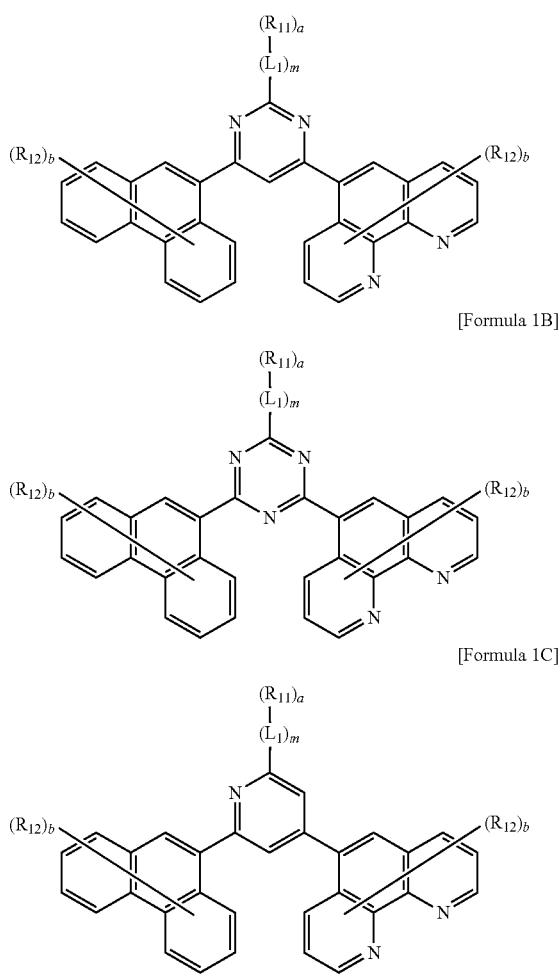

The compound of an embodiment represented by Formula 1A includes pyrimidine, and may include a structure in which number 4 and number 6 carbon atoms of pyrimidine are bonded to a carbon atom at position 5 or position 6 of 1,10-phenanthroline and a carbon atom at position 9 or position 10 of phenanthrene, respectively.

The compound of an embodiment represented by Formula 1B includes triazine, and may include a structure in which one carbon atom of triazine is bonded to a carbon atom at position 5 or position 6 of 1,10-phenanthroline, and another carbon atom that is not bonded to phenanthroline is bonded to a carbon atom at position 9 or position 10 of phenanthrene.

The compound of an embodiment represented by Formula 1C includes pyridine, and may include a structure in which one carbon atom of pyridine is bonded to a carbon atom at position 5 or position 6 of 1,10-phenanthroline, and another carbon atom that is not bonded to phenanthroline is bonded to a carbon atom at position 9 or position 10 of phenanthrene.

The synthesizing of a compound of an embodiment including a structure in which a nitrogen-containing ring is bonded to a carbon atom at position 5 or position 6 of 1,10-phenanthroline is relatively easier than the synthesizing of a compound that is bonded to a carbon atom at another position of 1,10-phenanthroline.

The synthesizing of a compound of an embodiment including a structure in which a nitrogen-containing ring is bonded to a carbon atom at position 9 or position 10 of phenanthrene is relatively easier than the synthesizing of a compound that is bonded to a carbon atom at another position of phenanthrene.

According to the bonding positions of the phenanthroline group and phenanthrene, the easiness of synthesis may vary. The bonding of a ring group to a carbon atom at position 5 or position 6 of 1,10-phenanthroline, or a carbon atom at position 9 or position 10 of phenanthrene makes synthesis easy, but the bonding positions of the phenanthroline group and phenanthrene included in the compound of an embodiment are not limited thereto.

In Formulas 1A to 1C above, $R_{11}$, $R_{12}$, $R_{13}$, $L_1$, a to c, and m may be the same as defined in Formula 1.

The compound of an embodiment includes a ring group containing at least one nitrogen atom to attract electrons more strongly than a benzene ring group having no nitrogen atom due to relative electron deficiency, and may thus exhibit excellent electron transport ability. The direct bonding of phenanthrene and phenanthroline to a ring group containing at least one nitrogen atom may allow the control of an electron-accepting ability, and thus the rate of electron transport can be controlled. Accordingly, the use of the compound of an embodiment as a material for an organic electroluminescence device may contribute to improvement in driving voltage, efficiency, and life characteristics of a device. For example, the compound of an embodiment may be included in at least one selected from the electron transport region ETR (or the electron transport regions ETR-1, ETR-2) and the at least one charge generating layer CGL included in the organic electroluminescence device 10, and the compound of an embodiment may allow the organic electroluminescence device 10 to exhibit lower driving voltage, improved efficiency, and increased life characteristics all together.

The compound of an embodiment represented by Formula 1 may be represented by one of Compounds 1-1 to 1-26. For example, the organic electroluminescence device 10 of an embodiment may include at least one of the compounds represented by Compounds 1-1 to 1-26 in at least one selected from the electron transport region ETR (or the electron transport regions ETR-1, ETR-2) and the charge generating layer CGL.

1-1

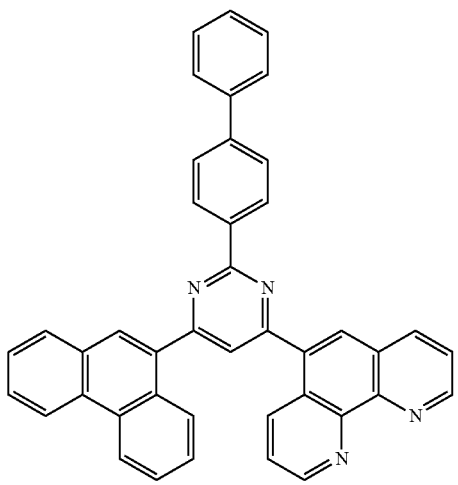

-continued
1-2
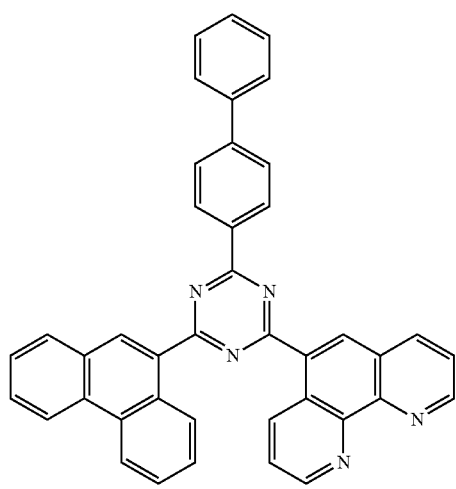
1-3
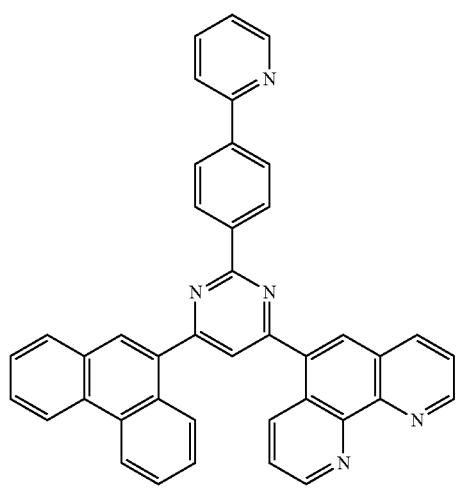
1-4
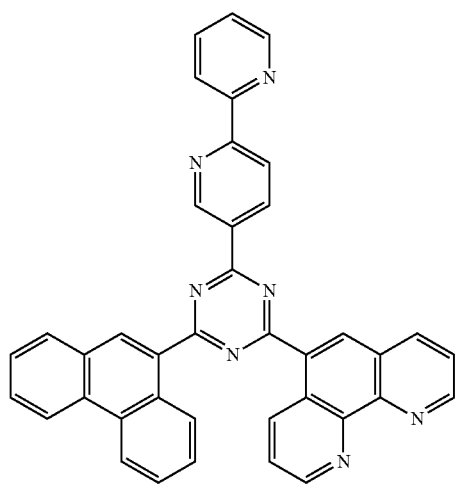
-continued
1-5
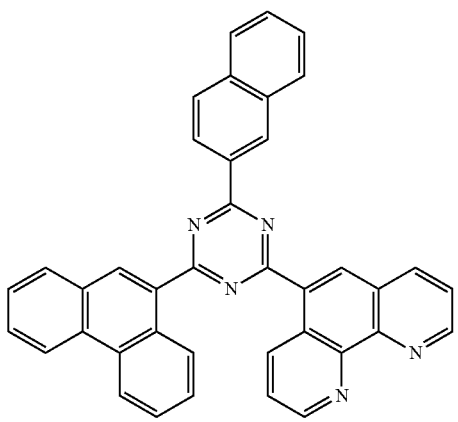
1-6
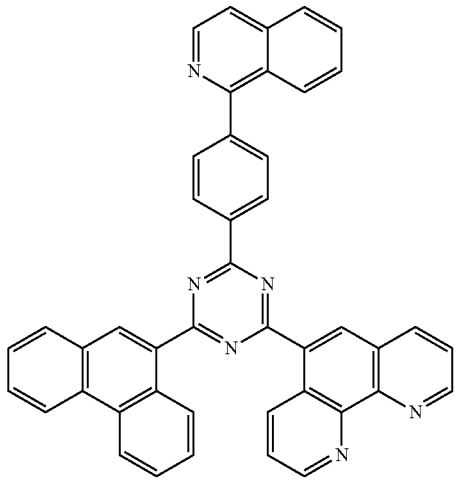
1-7
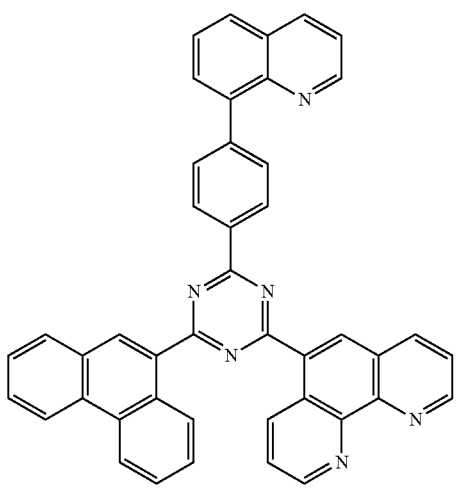

1-8
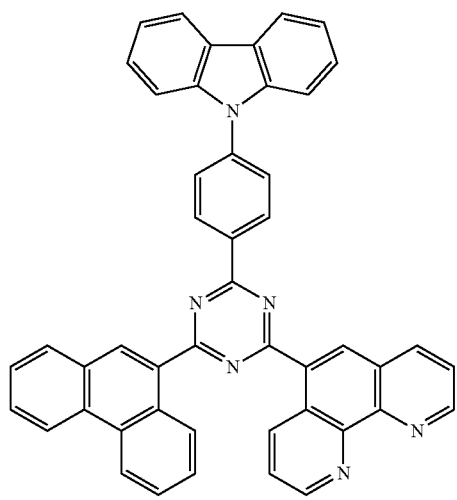
1-9
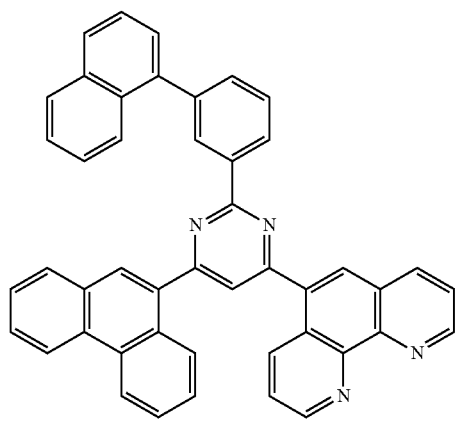
1-10
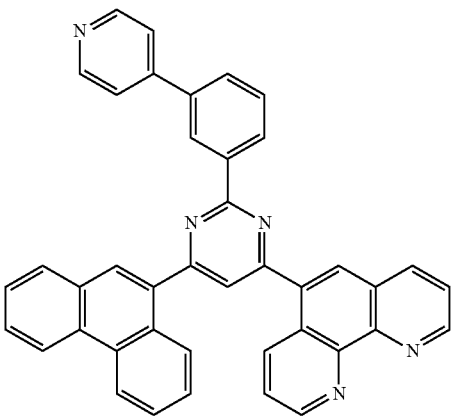
1-11
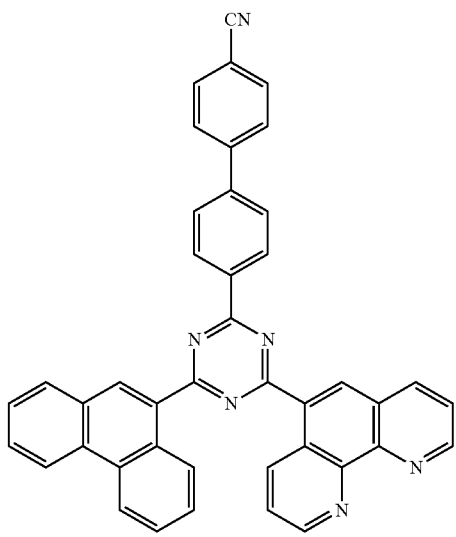
1-12
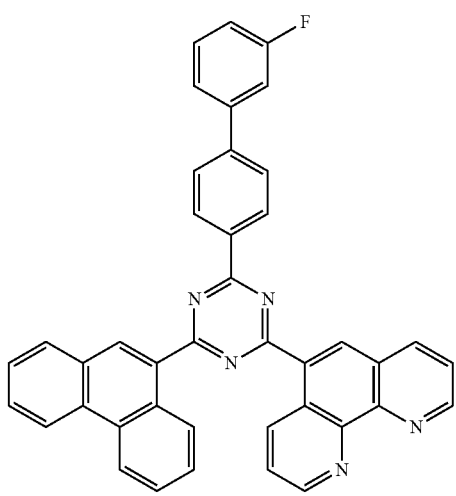
1-13
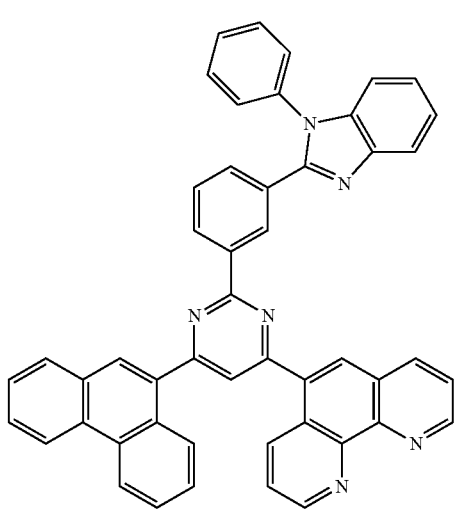

-continued
1-14
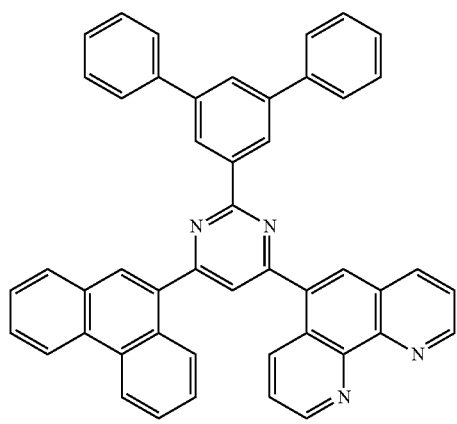
1-15
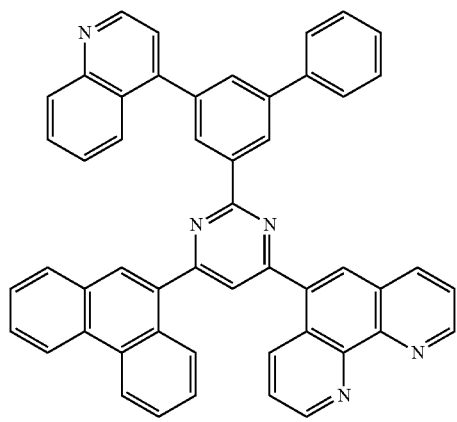
1-16
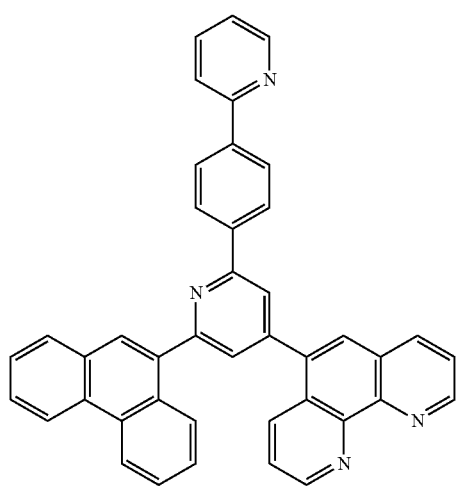
-continued
1-17
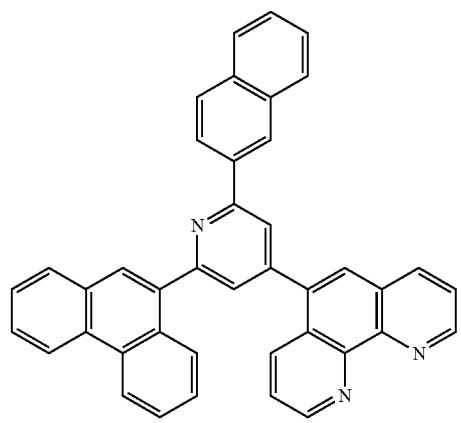
1-18
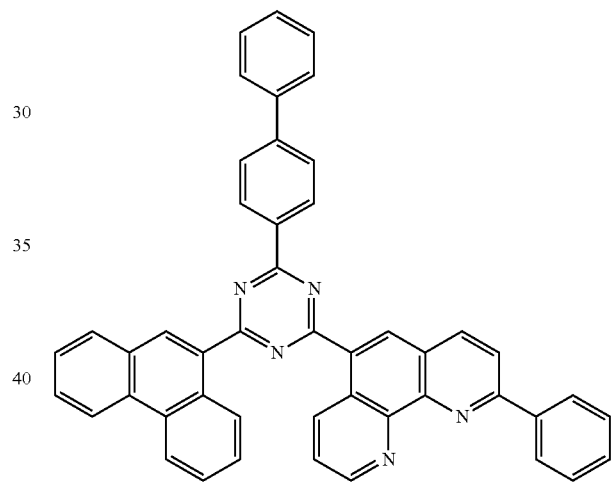
1-19
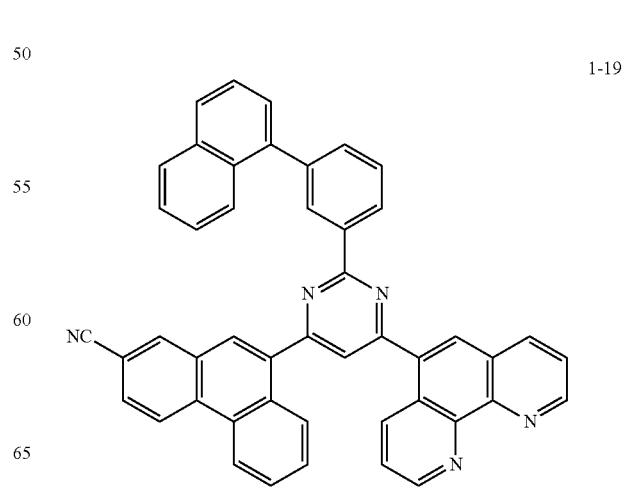

1-20
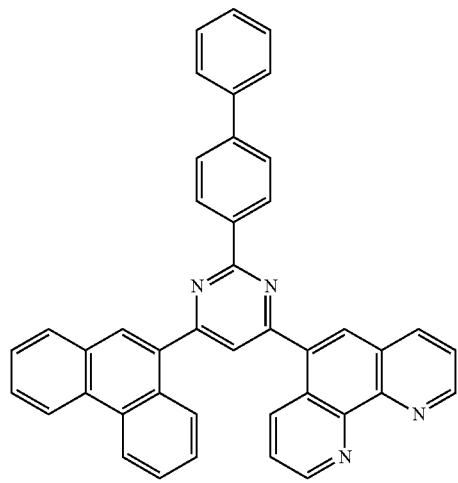
1-21
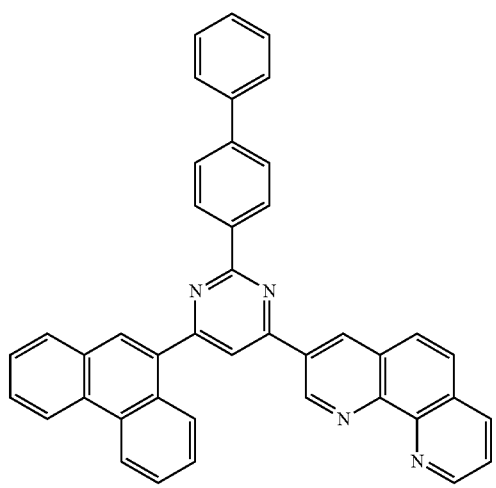
1-22
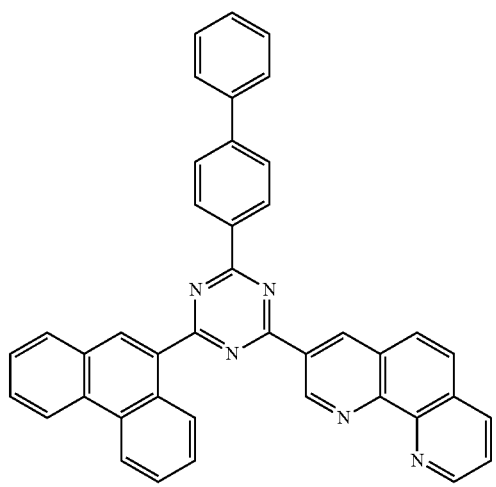
1-23
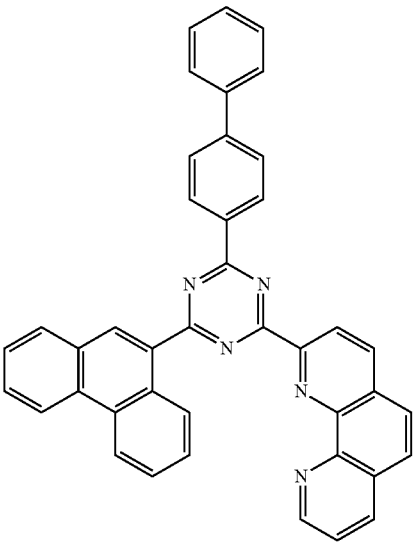
1-24
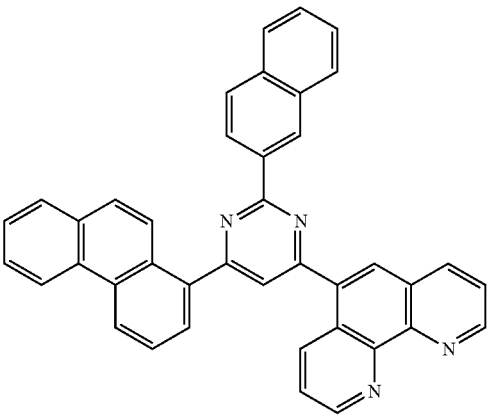
1-25
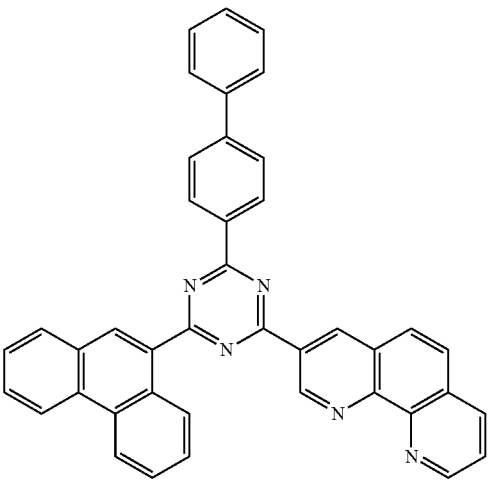

1-26

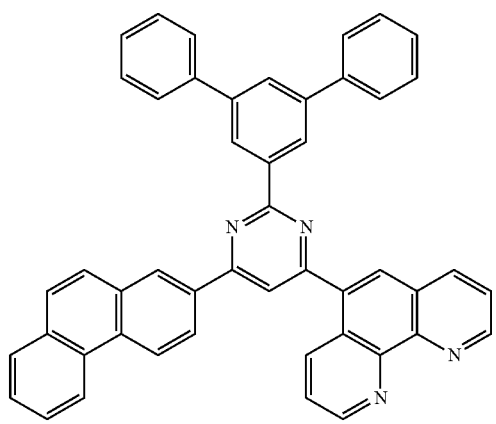

In the organic electroluminescence device 10 of an embodiment, when the electron transport region ETR includes multiple layers, at least one of the layers included in the electron transport region ETR may include the compound represented by Formula 1 of an embodiment described above. For example, the electron transport region ETR of an embodiment may include at least one of the electron transport layer ETL, the electron injection layer EIL, and the hole blocking layer HBL, and the compound represented by Formula 1 of an embodiment may be included in at least one of the layers included in the electron transport region ETR.

In the organic electroluminescence device 10 of an embodiment shown in FIGS. 1 to 5, the electron transport region ETR may further include a known material in addition to the compound represented by Formula 1. When the electron transport region ETR include multiple layers, a layer without containing the compound of an embodiment among the layers may include a known electron injection material, a known electron transport material, or a known hole blocking material. A layer containing the compound of an embodiment may further include a known electron injection material, a known electron transport material, or a known hole blocking material.

When the electron transport region ETR include the electron transport layer ETL, the electron transport layer ETL may include the compound of an embodiment represented by Formula 1 described above or a known material in the art. The electron transport region ETR may include an anthracene-based compound. However, embodiments of the inventive concept are not limited thereto, and the electron transport regions may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebg2), 9,10-di(naphthalene-2-yl)anthracene (ADN), 1,3-bis[3,5-di(pyridin-3-yl)phenyl]benzene (BmPyPhB) or a mixture thereof.

The electron transport regions ETR, ETR-1, and ETR-2 may include pyrimidine-based or triazine-based compounds. For example, the electron transport regions ETR, ETR-1, and ETR-2 may include compounds E1-1 to E1-7. However, compounds that may be included in the electron transport region ETR are not limited to the compounds below.

E1-1

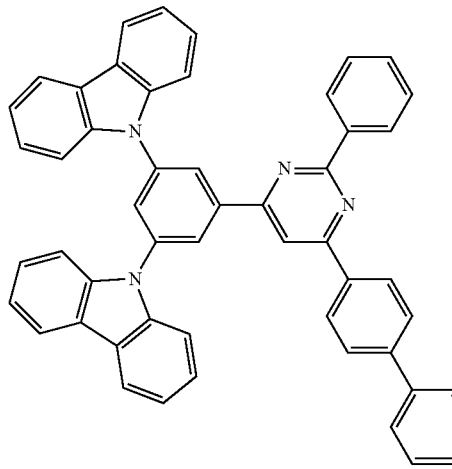

E1-2

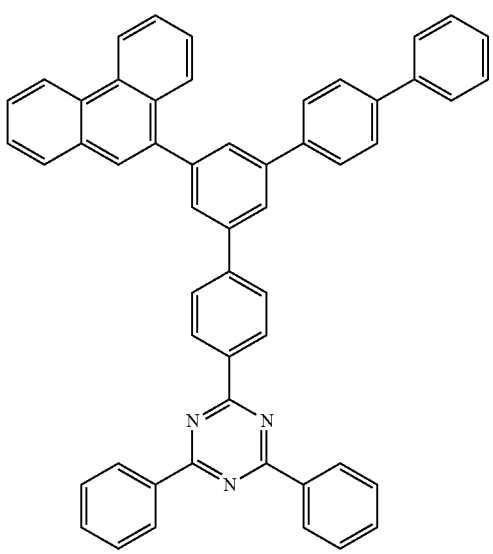

E1-3

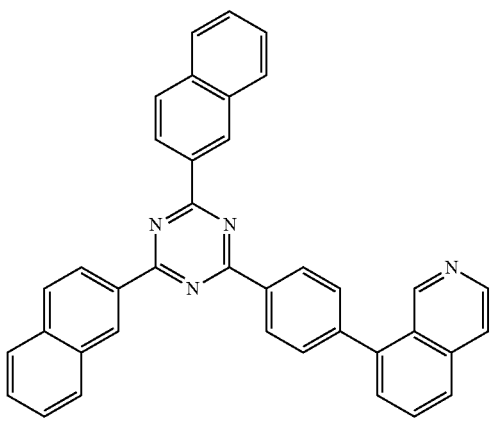

E1-4

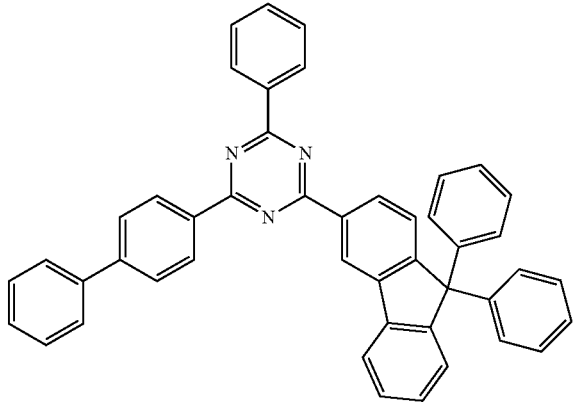

E1-5

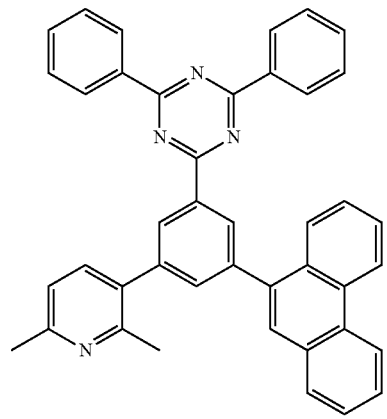

E1-6

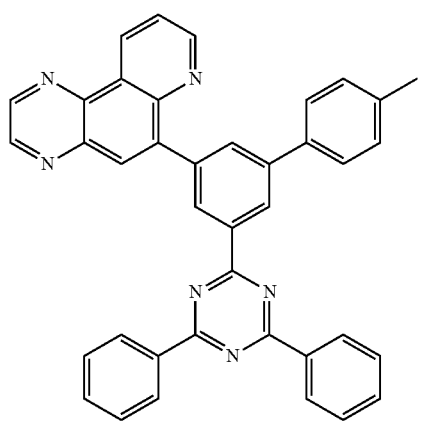

E1-7

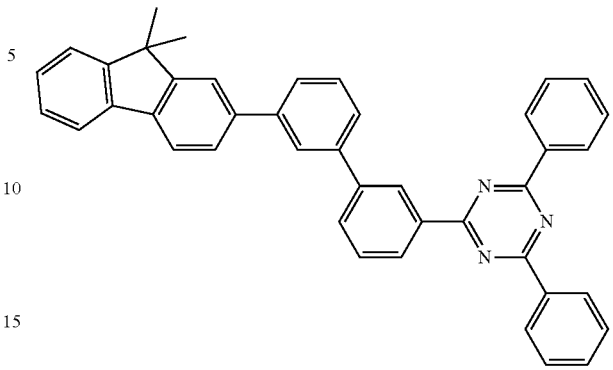

The thickness of the electron transport layers ETL may be in a range of about 100 Å to about 1,000 Å. For example, the thickness of the electron transport layers ETL may be in a range of about 150 Å to about 500 Å. When the thickness of the electron transport layers ETL satisfies the above-described range, satisfactory electron transport properties may be obtained without a substantial increase in driving voltage.

When the electron transport region ETR includes the electron injection layer EIL, the electron transport region ETR may include the compound of an embodiment represented by Formula 1 described above. The electron transport region ETR may be a halogenated metal such as LiF, NaCl, CsF, RbCl, RbI, and KI, a lanthanide metal such as Yb, combination materials of a halogenated metal and a lanthanide metal such as KI:Yb and RbI:Yb, a metal oxide such as $Li_2O$ and BaO, or lithium quinolate (LiQ), but is not limited thereto. The electron injection layer EIL may also be formed of a mixture material of an electron transport material and an insulating organo-metal salt. The organo-metal salt may be a material having an energy band gap of about 4 eV or more. For example, the organo-metal salt may include metal acetates, metal benzoates, metal acetoacetates, metal acetylacetonates, or metal stearates. The thickness of the electron injection layers EIL may be in a range of about 1 Å to about 100 Å. For example, the thickness of the electron injection layers EIL may be in a range of about 3 Å to about 90 Å. When the thickness of the electron injection layers EIL satisfies the above-described range, satisfactory electron injection properties may be obtained without a substantial increase in driving voltage.

As described above, the electron transport region ETR may include a hole blocking layer HBL. The hole blocking layer HBL may include the compound of an embodiment represented by Formula 1 described above. The hole blocking layer HBL may include other compounds in addition to the compound of an embodiment represented by Formula 1 described above. For example, at least one of 2,9-dimethyl-4,7-diphenyl-1,10-phenanthroline (BCP) or 4,7-diphenyl-1,10-phenanthroline (Bphen) may be included, but embodiments of the inventive concept are not limited thereto.

The hole transport region HTR is provided on the first electrode EL1. The hole transport region HTR may include at least one of the hole injection layer HIL, the hole transport layer HTL, the hole buffer layer (not shown), and the electron blocking layer EBL. The thickness of the hole transport regions HTR may be, for example, about 50 Å to about 15,000 Å.

The hole transport regions HTR may have a single layer formed of a single material, a single layer formed of different materials, or a multilayer structure including layers formed of different materials.

For example, the hole transport regions HTR may have a single layer structure of a hole injection layer HIL or a hole transport layer HTL, and may have a single layer structure formed of a hole injection material and a hole transport material. For example, the hole transport region HTR may have a single layer structure formed of different materials. The hole transport region HTR may have a structure in which a hole injection layer HIL/hole transport layer HTL, a hole injection layer HIL/hole transport layer HTL/hole buffer layer (not shown), a hole injection layer HIL/hole buffer layer (not shown), a hole transport layer HTL/hole buffer layer, or a hole injection layer HIL/hole transport layer HTL/electron blocking layer EBL are stacked in order from the first electrode EL1, but embodiments are not limited thereto.

The hole transport regions HTR, HTR-1 and HTR-2 may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include an amine compound. For example, the hole transport region HTR may include compounds H1-1 to H1-5. However, an amine compound that may be included in the hole transport region HTR is not limited to the compounds below.

H1-1

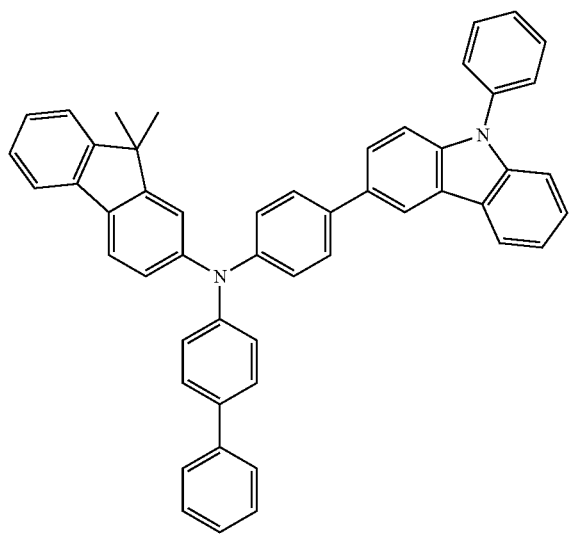

H1-2

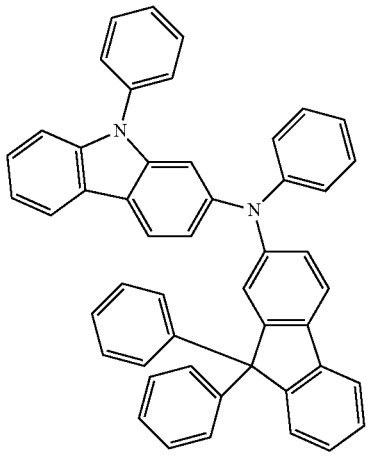

H1-3

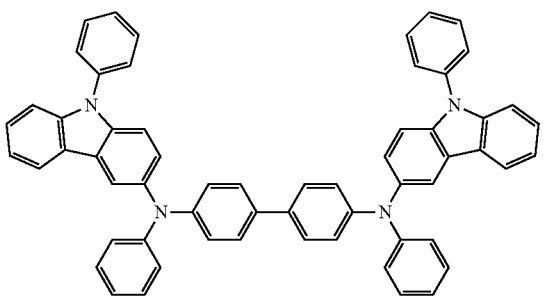

H1-4

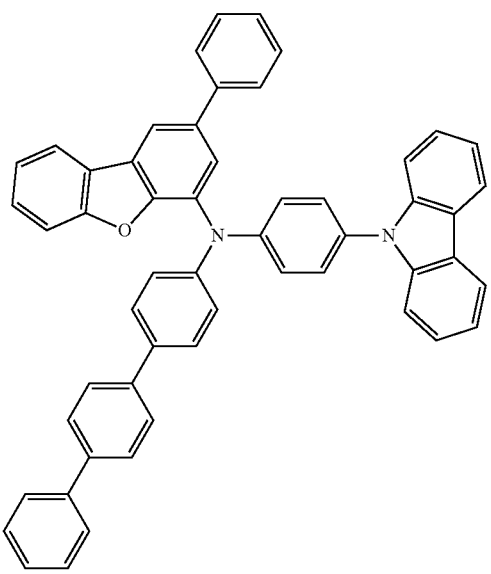

H1-5

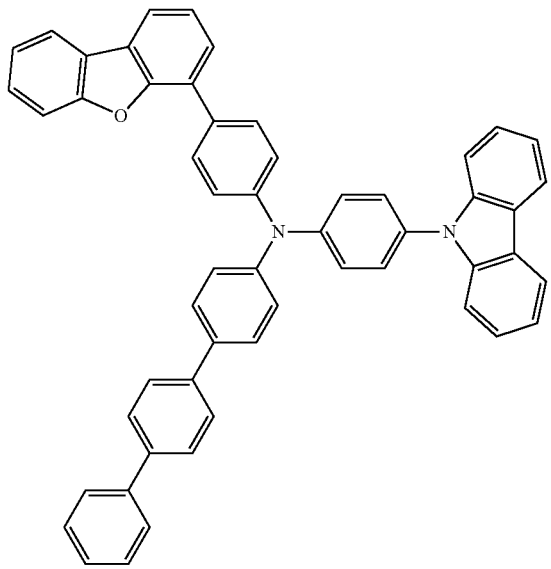

In the organic electroluminescence device 10 of an embodiment, the hole injection layer HIL may include a conventional hole injection material. The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4''-[tris(3-methylphenyl)phenylamino]triphenylamine] (m-MTDATA), 4,4',4''-tris(N,N-diphenylamino)triphenylamine (TDATA), 4,4',4''-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f:2',3'-h]quinoxaline-2,3,6,7,10,11-hexacarbonitrile (HAT-CN), etc.

In the organic electroluminescence device 10 of an embodiment, the hole transport layer HTL may include a conventional hole transport material. The hole transport layer HTL may include, for example, carbazole-based derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphtalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis(N-carbazolyl)benzene (mCP), etc.

As described above, in the organic electroluminescence device 10 of an embodiment, the hole transport region HTR may further include at least one of the hole buffer layer (not shown) or the electron blocking layer EBL in addition to the hole injection layer HIL and the hole transport layer HTL. The hole buffer layer (not shown) may compensate for a resonance distance according to the wavelength of light emitted from an emission layer EML to increase light emission efficiency. Materials which may be included in the hole buffer layer (not shown) may be used as materials which may be included in the hole transport region HTR.

When the hole transport region HTR further includes the electron blocking layer EBL disposed between the hole transport layer HTL and the emission layer EML, the electron blocking layer EBL may serve to prevent electrons from being injected from the electron transport region ETR to the hole transport region HTR.

In the organic electroluminescence device 10 of an embodiment, when the hole transport region HTR include the electron blocking layer EBL, the electron blocking layer EBL may include a conventional material known in the art. The electron blocking layer EBL may include, for example, carbazole-based derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine derivatives such as 4,4',4''-tris(N-carbazolyl)triphenylamine (TCTA), N,N'-di(naphthalene-1-yl)-N,N'-diplienyl-benzidine (NPB), 4,4-cyclohexylidene bis[N,N-bis(4-methylphenyl)benzenamine] (TAPC), 4,4'-bis[N,N'-(3-tolyl)amino]-3,3'-dimethylbiphenyl (HMTPD), 9-(4-tert-Butylphenyl)-3,6-bis(triphenylsilyl)-9H-carbazole (CzSi), 9-phenyl-9H-3,9'-bicarbazole (CCP), 1,3-Bis(N-carbazolyl)benzene (mCP), or 1,3-bis(1,8-dimethyl-9H-carbazol-9-yl)benzene (mDCP), etc.

The thickness of the hole transport regions HTR, HTR-1, and HTR-2 may be in a range of about 100 Å to about 10,000 Å. For example, the thickness of the hole transport regions HTR, HTR-1, and HTR-2 may be in a range of about 100 Å to about 5,000 Å. The thickness of the hole injection region HIL may be, for example, in a range of about 30 Å to about 1,000 Å. The thickness of the hole transport layer HTL may be in a range of about 30 Å to about 1,000 Å. For example, the thickness of the electron blocking layer EBL may be in a range of about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without a substantial increase in driving voltage.

The hole transport region HTR may further include, in addition to the above-described materials, a charge generating material to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, but is not limited thereto. For example, non-limiting examples of the p-dopant may include quinone derivatives such as tetracyanoquinodimethane (TCNQ) and 2,3,5,6-tetrafluoro-7,7,8,8-tetracyanoquinodimethane (F4-TCNQ), metal oxides such as tungsten oxide and molybdenum oxide, etc., but are not limited thereto.

The emission layer EML is provided on the hole transport region HTR. The thickness of the emission layer EML may be in a range of about 100 Å to about 1000 Å. For example, the thickness of the emission layer EML may be in a range of about 100 Å to about 400 Å. The emission layers EML may have a single layer formed of a single material, a single layer formed of different materials, or a multilayer structure having layers formed of different materials.

The emission layer EML (or each of the emission layers EML-1 and EML-2) may emit one of red, green, blue, white, yellow, or cyan light. The emission layer EML (or each of the emission layers EML-1 and EML-2) may include a fluorescence light emitting material or a phosphorescent light emitting material.

In the organic electroluminescence device 10 of an embodiment, the emission layer EML may include an anthracene derivative, a pyrene derivative, a fluoranthene derivative, a chrysene derivative, a dihydrobenzanthracene derivative, or a triphenylene derivative. To be specific, the emission layers EML may include an anthracene derivative represented by Formula 2. The emission layers EML may include a compound represented by Formula 2 as a fluorescence host material.

[Formula 2]

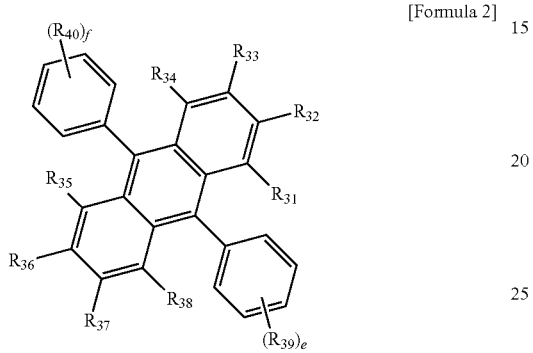

In Formula 2, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or bonded to an adjacent group to form a ring. In Formula 2, $R_{31}$ to $R_{40}$ may be bonded to an adjacent group to form a saturated hydrocarbon ring or unsaturated hydrocarbon ring.

In Formula 2, e and f may each independently be an integer from 0 to 5.

Formula 2 may be represented by one of Compounds 2-1 to 2-16.

2-1

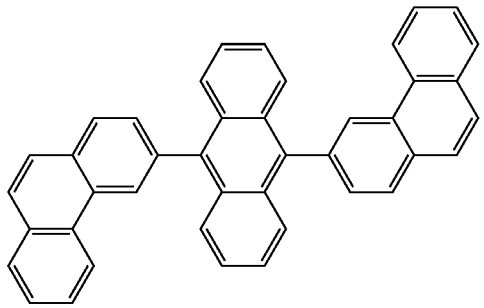

2-2

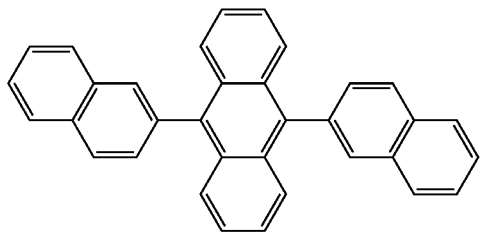

2-3

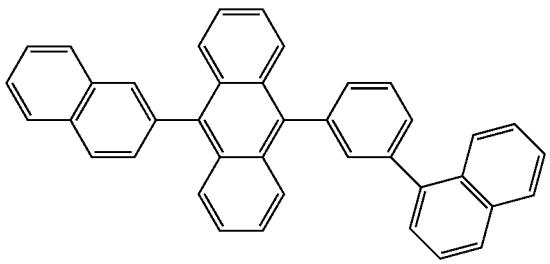

2-4

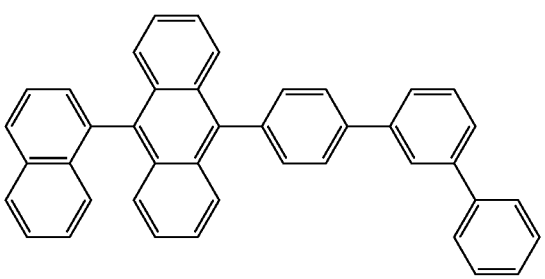

2-5

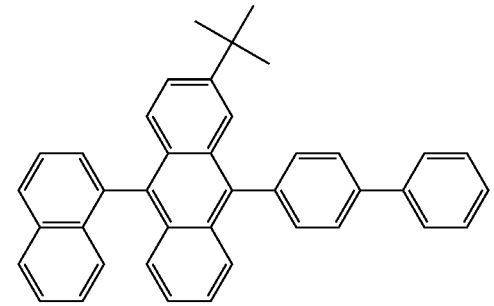

2-6

2-7

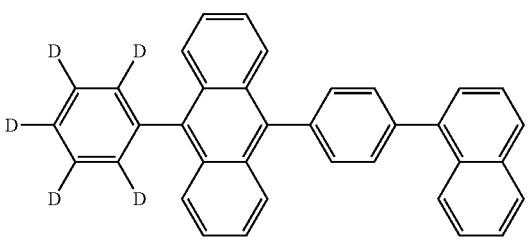

2-8
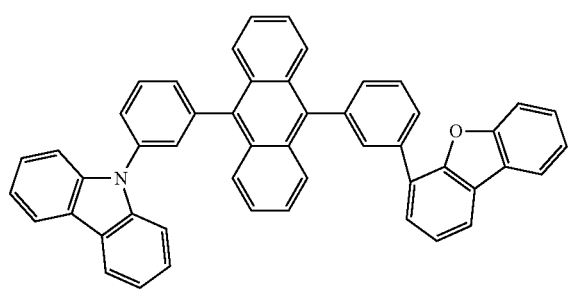

2-9
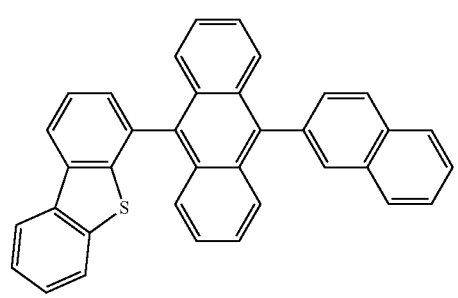

2-10
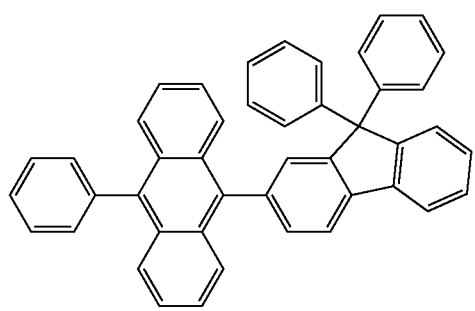

2-1
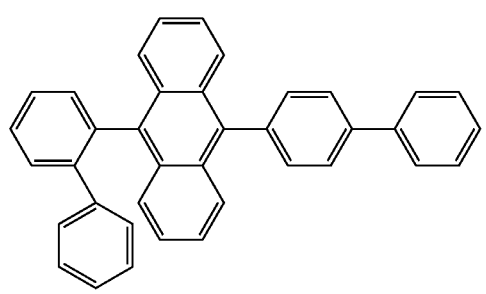

2-12
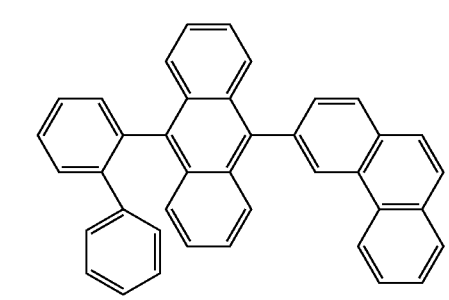

2-13
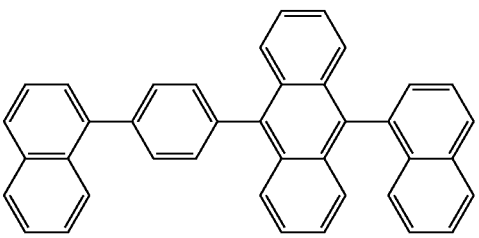

2-14
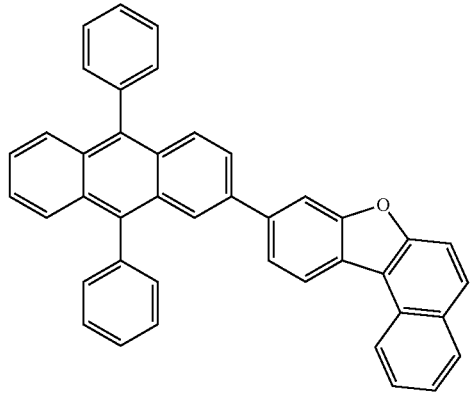

2-15
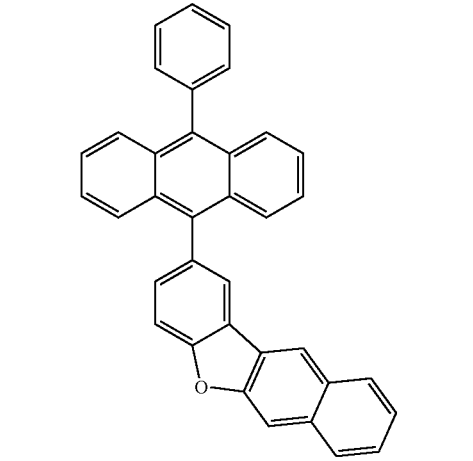

2-16
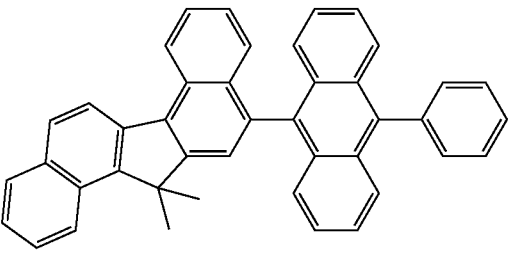

In the organic electroluminescence device 10 of an embodiment shown in FIGS. 1 to 4, the emission layers EML may include a host and a dopant.

In an embodiment, the emission layer EML may further include a general material known in the art as a host material. For example, the emission layer EML may include, as a host material, tris(8-hydroxyquinolinato)aluminum (Alq$_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris (carbazol sol-9-yl) triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzo[b,d]furan (PPF), 3,3'-bis(N-carbazolyl)-1,1'-biphenyl (mCBP), 1,3-bis(carbazolyl-9-yl)benzene (mCP), etc.

In an embodiment, the emission layer EML may include a carbazole-based compound as a phosphorescent host material. For example, the emission layer EML may include compounds EM1-1 to EM1-4. However, a phosphorescent host material that may be included in the emission layer EML is not limited to compounds below.

EM1-1

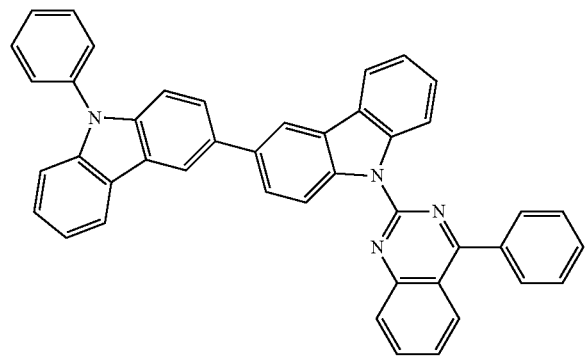

EM1-2

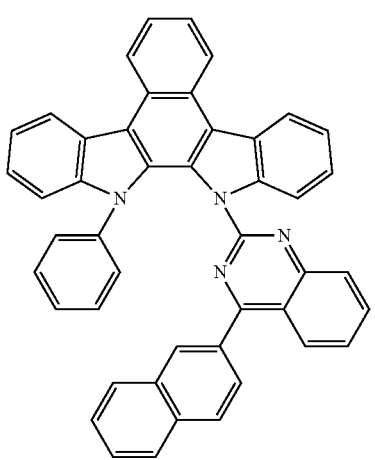

EM1-3

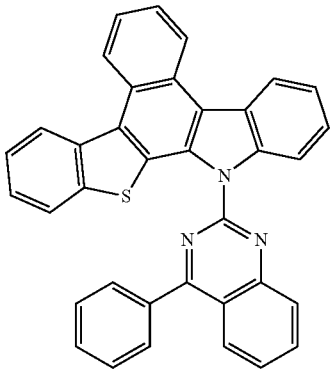

EM1-4

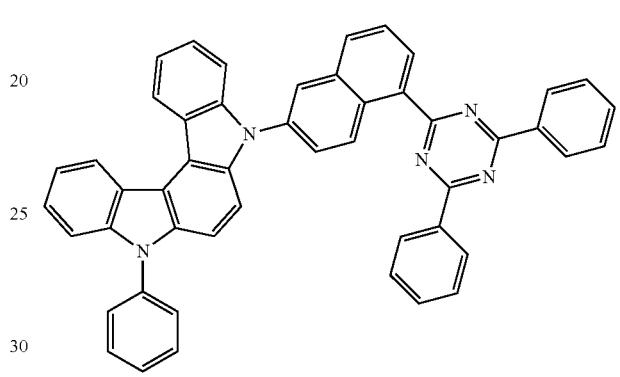

In the organic electroluminescence device 10 of an embodiment, the emission layer EML may include, as a dopant, styryl derivatives (e.g., 1,4-bis[2-(3-N-ethylcarbazoyl)vinyl]benzene (BCzVB), 4-(di-p-tolylamino)-4"-[(di-p-tolylamino)styryl]stilbene (DPAVB), and N-(4-((E)-2-(6-((E)-4-(diphenylamino)styryl)naphthalen-2-yl)vinyl) phenyl)-N-phenylbenzenamine (N-BDAVBi), perylene and the derivatives thereof (e.g., 2,5,8,11-tetra-t-butylperylene (TBP), pyrene and the derivatives thereof (e.g., 1,1-dipyrene, 1,4-dipyrenylbenzene, 1,4-bis(N,N-diphenylamino)pyrene, etc.

The emission layer EML may include a polycyclic compound of an embodiment and a known phosphorescent dopant material. For example, as a phosphorescent dopant, a metal complex including iridium (Ir), platinum (Pt), osmium (Os), gold (Au), titanium (Ti), zirconium (Zr), hafnium (Hf), europium (Eu), and terbium (Tb), or thulium (Tm) may be used. To be specific, a phosphorescent dopant including platinum octaethyl porphyrin (PtOEP) or iridium (III) bis(4,6-difluorophenylpyridinato-N,C2') (FIrpic), which is an iridium organometallic complex, bis(2,4-difluorophenylpyridinato))-tetrakis(1-pyrazolylyl)borate iridium (III) (Fir6), etc. may be used, but embodiments of the inventive concept are not limited thereto.

The emission layer EML may further include a known phosphorescent host material, for example, bis(4-(9H-carbazol-9-yl)phenyl)diphenylsilane (BCPDS).

When the emission layer EML emit red light, the emission layer EML may further include, for example, a fluorescent material including PBD:Eu (DBM)$_3$(Phen)(tris(dibenzoylmethanato)phenanthoroline europium) or perylene. When the emission layer EML emit red, a dopant included in the emission layer EML may be, for example, a metal complex such as bis(1-phenylisoquinoline) acetylacetonate iridium (PIQIr(acac)), bis(1-phenylquinoline) acetylacetonate iridium (PQIr(acac)), tris(1-phenylquinoline) iridium (PQIr) and octaethylporphyrin platinum (PtOEP), or an organometallic complex, rubrene and derivatives thereof, and 4-dicyanomethylene-2-(p-dimethylaminostyryl)-6-methyl-4H-pyran (DCM) and derivatives thereof.

When the emission layer EML emit green light, the emission layer EML may further include a fluorescent material including, for example, tris(8-hydroxyquinolino) aluminum ($Alq_3$). When the emission layer EML emit green, a dopant included in the emission layer EML may be, for example, a metal complex such as $Ir(ppy)_3$fac-tris(2-phenylpyridine)iridium or an organometallic complex, and coumarin and derivatives thereof.

When the emission layer EML emit blue light, the emission layer EML may further include a fluorescent material including any one selected from the group consisting of, for example, spiro-DPVBi, spiro-6P, distyryl-benzene (DSB), distyryl-arylene (DSA), polyfluorene-based polymer (PFO), and poly(p-phenylene vinylene)-based polymer (PPV). When the emission layer EM emit blue, a dopant included in the emission layer EML may be, for example, a metal complex such as (4,6-F2ppy)2Irpic or an organometallic complex, perylene and derivatives thereof, a diamine compound bonded to a fused ring, a diamino pyrene-based compound, a boron-based compound and derivatives thereof.

The emission layers EML, EML-1, and EML-2 of the inventive concept may include a quantum dot material. The core of the quantum dot may include a Group II-VI compound, a Group III-VI compound, a Group III-V compound, a Group IV-VI compound, a Group IV element or compound, a Group I-III-IV compound, or a combination thereof.

The Group II-VI compound may be selected from the group consisting of a binary compound selected from the group consisting of CdS, CdSe, CdTe, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-IV compound may include a binary compound such as $In_2S_3$ and $In_2Se_3$, a ternary compound such as $InGaS_3$ and $InGaSe_3$, or any combination thereof.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, GaAlNP, and a mixture thereof, and a quaternary compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V semiconductor compound may further include a Group II metal such as InZnP.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

The Group I-III-VI semiconductor compound may include a ternary compound such as AgInS, $AgInS_2$, CuInS, $CuInS_2$, $CuGaO_2$, $AgGaO_2$, $AgAlO_2$, or any combination thereof.

A binary compound, a ternary compound, or a quaternary compound may be present in a particle with a uniform concentration distribution, or may be present in the same particle with a partially different concentration.

A quantum dot may have a core/shell structure including a core and a shell surrounding the core. The quantum dot may have a core/shell structure in which one quantum dot surrounds another quantum dot. An interface between a core and a shell may have a concentration gradient in which the concentration of an element present in the shell becomes lower toward the center.

In some embodiments, a quantum dot may have a core/shell structure including a core having nano-crystals and a shell surrounding the core described above. The shell of the quantum dot may serve as a protection layer to prevent the chemical deformation of the core so as to maintain semiconductor properties, and/or a charging layer to impart electrophoresis properties to the quantum dot. The shell may be a single layer or a multilayer. An interface between the core and the shell may have a concentration gradient in which the concentration of an element present in the shell becomes lower toward the center. An example of the quantum dot shell may be a metal or non-metal oxide, a semiconductor compound, or a combination thereof.

For example, the metal or non-metal oxide used in the shell may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and NiO, or a ternary compound such as $MgAl_2O_4$, $CoFe_2O_4$, $NiFe_2O_4$, and $CoMn_2O_4$ but embodiments of the inventive concept are not limited thereto.

The semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the inventive concept are not limited thereto.

A quantum dot may have a full width of half maximum (FWHM) of a light emitting wavelength spectrum equal to or less than about 45 nm. For example, a quantum dot may have a FWHM of light emitting wavelength spectrum equal to or less than about 40 nm. For example, a quantum dot may have a FWHM of light emitting wavelength spectrum equal to or less than about 30 nm. Color purity or color reproducibility may be improved in the above range. Light emitted through such a quantum dot may be emitted in all directions so that a wide viewing angle may be improved.

The form of a quantum dot is not particularly limited as long as it is a form commonly used in the art. For example, a quantum dot in the form of spherical, pyramidal, multi-arm, or cubic nanoparticles, nanotubes, nanowires, nanofibers, nanoparticles, etc. may be used.

A quantum dot may control the color of emitted light according to the particle size thereof and thus the quantum dot may have various light emission colors such as green, red, etc.

A capping layer CPL may be further disposed on the second electrode EL2 of the organic electroluminescence device 10 of an embodiment. The capping layer CPL may include a multilayer or a single layer.

In an embodiment, the capping layer CPL may be an organic layer or an inorganic layer. For example, when the capping layer CPL includes an inorganic material, the inorganic material may include an alkali metal compound such as LiF, an alkaline earth metal compound such as $MgF_2$, SiON, $SiN_x$, $SiO_y$, etc.

For example, when the capping layer CPL includes an organic material, the organic material may include α-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol sol-9-yl)triphenylamine (TCTA), etc., or may include epoxy resins or acrylates such as methacrylate. However, embodiments of the inventive concept are not limited thereto, and compounds P1 to P5 may also be included.

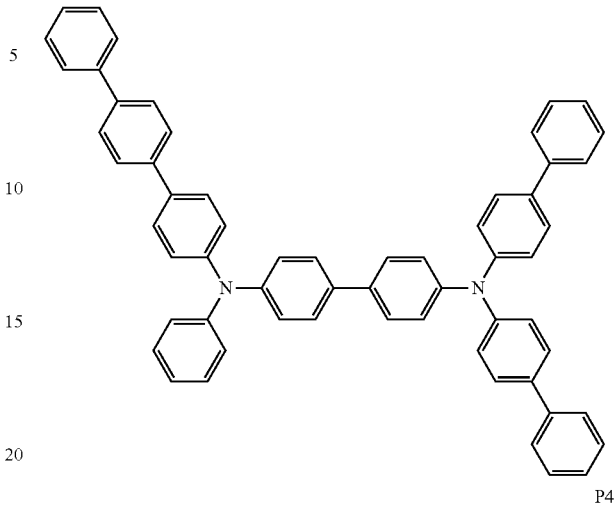

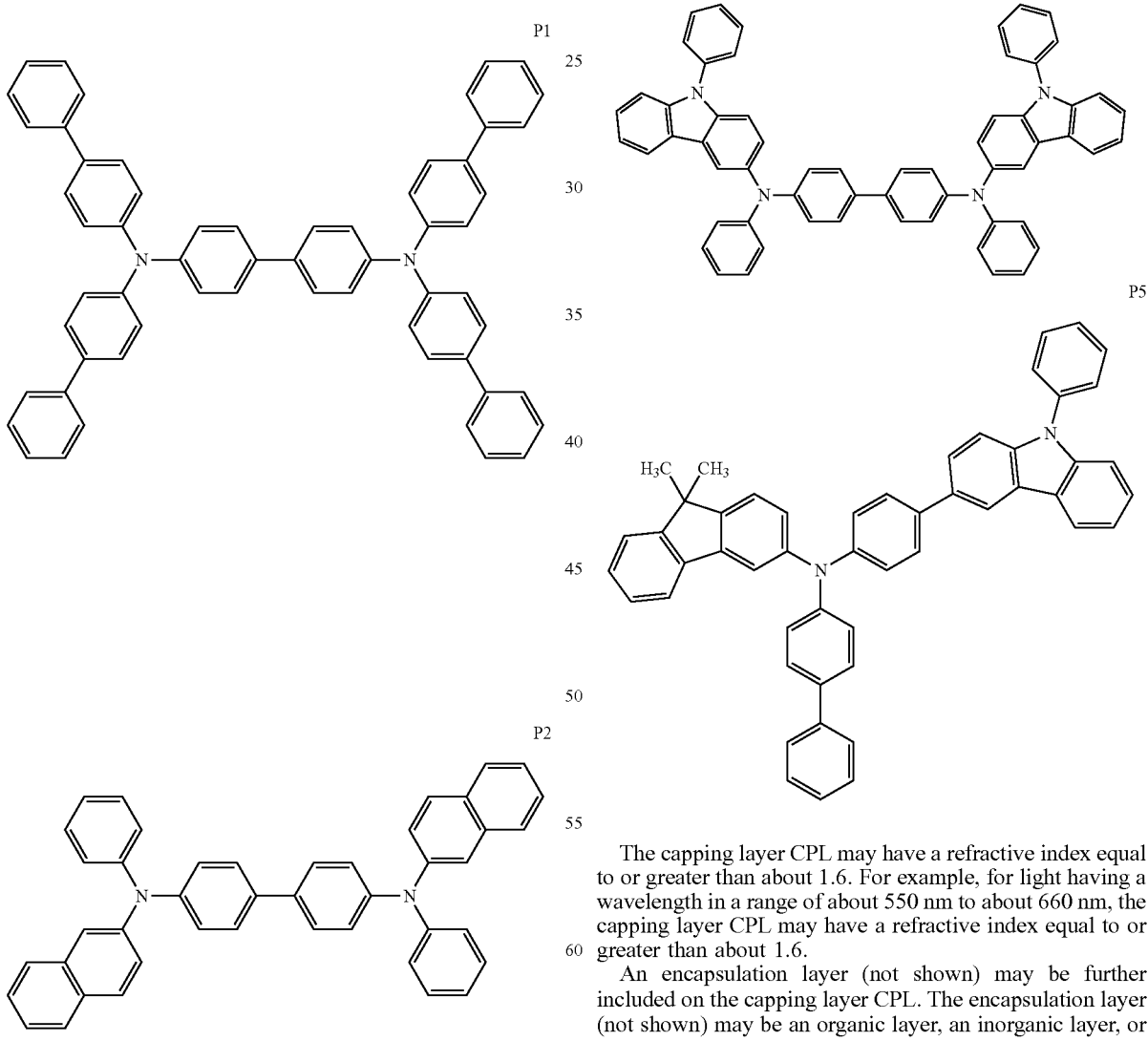

The capping layer CPL may have a refractive index equal to or greater than about 1.6. For example, for light having a wavelength in a range of about 550 nm to about 660 nm, the capping layer CPL may have a refractive index equal to or greater than about 1.6.

An encapsulation layer (not shown) may be further included on the capping layer CPL. The encapsulation layer (not shown) may be an organic layer, an inorganic layer, or a composite material layer. The encapsulation layer (not shown) may include at least one organic layer and at least one inorganic layer. The organic layer included in the encapsulation layer (not shown) may be a photopolymerizable compound, and may include, for example, an acrylic-based material or an epoxy-based material, etc. The inorganic layer included in the encapsulation layer (not shown) may include materials such as SiON, $SiO_x$, and $SiN_y$.

The organic electroluminescence device 10 according to an embodiment may include light emitting units LU-1 and LU-2. Each of the light emitting units LU-1 and LU-2 may include a hole transport region, an emission layer, and an electron transport region. Referring to FIG. 5, a first light emitting unit LU-1 may include a first hole transport region HTR-1, a first emission layer EML-1, and a first electron transport region ETR-1. A second light emitting unit LU-2 may include a second hole transport region HTR-2, a second emission layer EML-2, and a second electron transport region ETR-2. However, embodiments of the inventive concept are not limited thereto, and an organic electroluminescence element may include three or more light emitting units.

The same content as described above for the hole transport region, the emission layer, and the electron transport region may be applied to hole transport regions HTR-1 and HTR-2, emission layers EML-1 and EML-2, and electron transport regions ETR-1 and ETR-2 included in the organic electroluminescent device 10 of an embodiment, respectively.

The first hole transport region HTR-1 and the second hole transport region HTR-2 may include a same material, or may include different materials from each other. The first electron transport region ETR-1 and the second electron transport region ETR-2 may include a same material, or may include different materials from each other.

For example, the first electron transport region ETR-1 and the second electron transport region ETR-2 may include the compound of an embodiment represented by Formula 1 described above, and the first electron transport region ETR-1 and the second electron transport region ETR-2 both may further include a known material. The first electron transport region ETR-1 may include the compound of an embodiment described above, and the second electron transport region ETR-2 may include a known material. The first electron transport region ETR-1 may include the compound of an embodiment and further include a known material, and the second electron transport region ETR-2 may include a known material. The second electron transport region ETR-2 may include the compound of an embodiment and further include a known material, and the first electron transport region ETR-1 may include a known material.

The first emission layer EML-1 and the second emission layer EML-2 may emit different colors. For example, the first emission layer EML-1 may emit blue light, and the second emission layer EML-2 may emit red light or green light. For example, both the first emission layer EML-1 and the second emission layer EML-2 may emit light of a same color. However, embodiments of the inventive concept are not limited thereto.

For example, when the organic electroluminescence device of an embodiment includes three light emitting units, the three emission layers may emit a same color, or the three emission layers each may emit different colors. When the three emission layers each emit different colors, the organic electroluminescence device may emit white light. For example, in the organic electroluminescence device, two emission layers may emit a same color, and one emission layer may emit a different color. However, this is merely an example and is not limited to any one embodiment.

According to an embodiment, at least one charge generating layer CGL may be included between adjacent ones of light emitting units LU-1 and LU-2. For example, an organic electroluminescence device including three light emitting units may include two charge generating layers. The charge generating layer CGL may include the compound of an embodiment represented by Formula 1 described above.

The organic electroluminescence device 10 according to an embodiment of the inventive concept includes the compound of an embodiment represented by Formula 1 described above in at least one functional layer disposed between the first electrode EL1 and the second electrode EL2, and may thus exhibit improved driving voltage, light emission efficiency, and life characteristics. For example, the compound according to an embodiment may be included in the electron transport region ETR of the organic electroluminescence device 10 of an embodiment, and the organic electroluminescence device of an embodiment may exhibit low driving voltage, excellent light emission efficiency and long life characteristics.

The organic electroluminescence device 10 of an embodiment including the light emitting units LU-1 and LU-2 includes the compound of an embodiment represented by Formula 1 described above in at least one of selected from the at least one charge generating layer CGL and the electron transport regions ETR-1 and ETR-2, and may thus exhibit improved light emission efficiency and life characteristics.

The compound of an embodiment represented by Formula 1 described above includes an aromatic ring containing nitrogen at the center, for example, pyridine, pyrimidine or triazine, to relatively have less electrons than a benzene ring, and may thus obtain an excellent electron transport ability. The structure in which phenanthrene and phenanthroline are bonded in a central ring containing at least one nitrogen may allow the control of the rate of electron transport, and thus, the compound of an embodiment may contribute to low driving voltage, high efficiency and long life characteristics of the organic electroluminescence device.

Hereinafter, with reference to Examples and Comparative Examples, a compound according to an embodiment of the inventive concept and an organic electroluminescence device of an embodiment will be described in detail. The Examples shown below are illustrated only for the understanding of the inventive concept, and the scope of the inventive concept is not limited thereto

EXAMPLES

1. Synthesis of Compounds

A process of synthesizing a compound according to an embodiment will be described in detail by explaining a process of synthesizing Compounds 1-1, 1-4, 1-11, and 1-14. A process of synthesizing a compound, which will be described hereinafter, is provided as an example, and thus a process of synthesizing a compound according to an embodiment of the inventive concept is not limited to Examples below.

<Synthesis of Compound 1-1>

Compound 1-1 according to an embodiment may be synthesized by, for example, Reaction Formula 1 below.

[Reaction Formula 1]

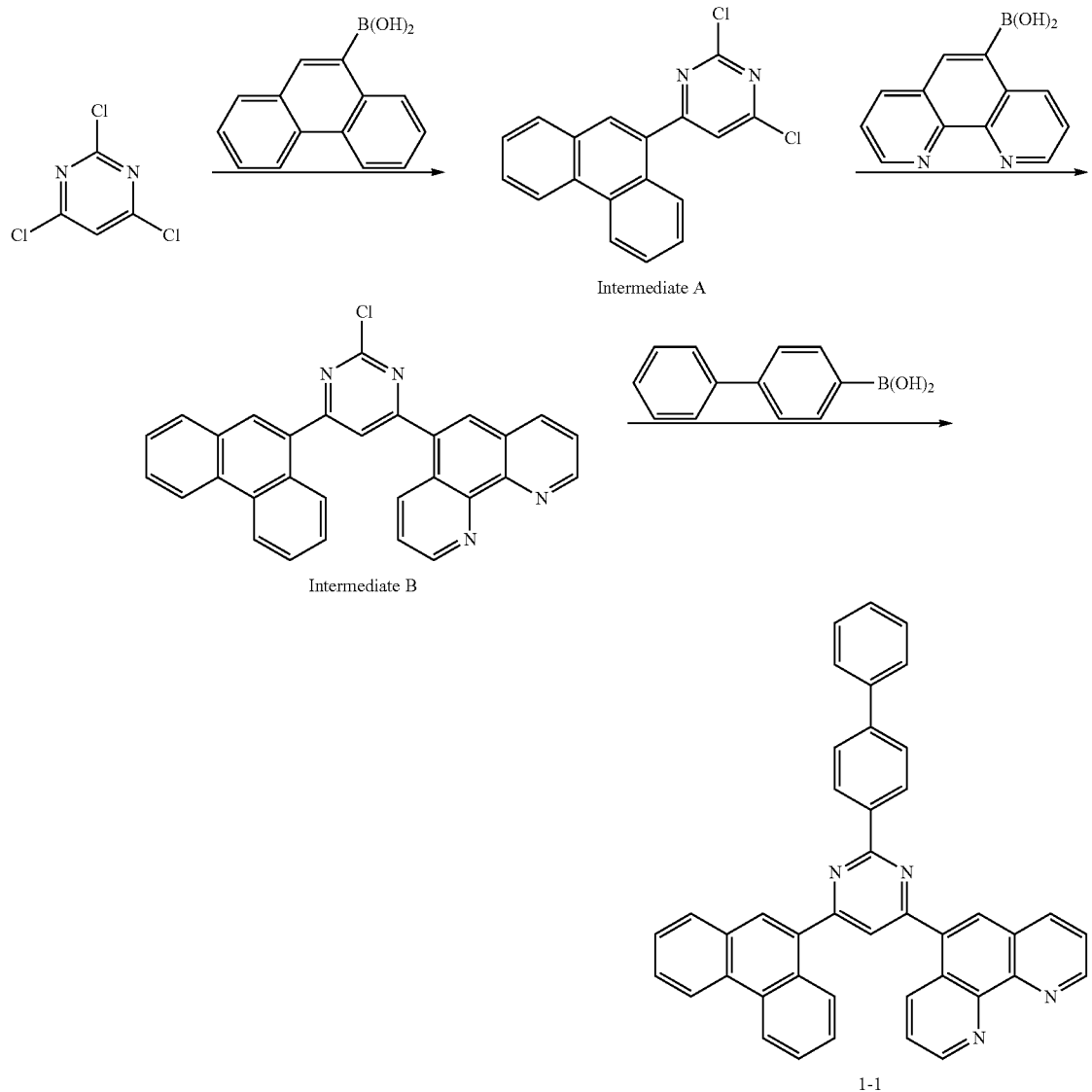

(Synthesis of Intermediate A)

2,4,6-trichloropyrimidine (1.8 g, 10 mmol), phenanthren-9-ylboronic acid (2.4 g, 11 mmol), K$_2$CO$_3$ (2.8 g, 20 mmol), and Pd(PPh$_3$)$_4$ (0.41 g, 0.35 mmol) were put into a Schlenk tube, dried under vacuum for 2 hours, and dissolved in THF (100 mL). N$_2$-purged anhydrous EtOH (20 mL) was added and the mixture was stirred at 80° C. for 2 hours under nitrogen. The resultant was cooled at room temperature, washed with excess DCM and distilled water after a solvent is removed under reduced pressure, and an organic layer is separated. The separated organic layer was dried with MgSO$_4$ and purified by column chromatography (dichloromethane/hexane, 2:1, v/v) to obtain 2,4-dichloro-6-(phenanthren-9-yl)pyrimidine (A) 2.4 g (7.5 mmol, yield 75%)

Synthesis of Intermediate B

Intermediate A (3.3 g, 10 mmol), (1,10-phenanthrolin-5-yl)boronic acid (2.6 g, 12 mmol), K$_2$CO$_3$ (2.8 g, 20 mmol), and Pd(PPh$_3$)$_4$ (0.41 g, 0.35 mmol) were put into a Schlenk tube, dried under vacuum for 2 hours, and dissolved in DMF (100 mL). N$_2$-purged anhydrous EtOH (20 mL) was added and the mixture was stirred at 100° C. for 48 hours under nitrogen. The resultant was cooled at room temperature, washed with excess DCM and distilled water after a solvent is removed under reduced pressure, and an organic layer is separated. The separated organic layer was dried with MgSO$_4$ and purified by column chromatography (DCM) to obtain 5-(2-chloro-6-(phenanthren-9-yl)pyrimidin-4-yl)-1,10-phenanthroline (B) 3.2 g (6.8 mmol, yield 68%).

Synthesis of Compound 1-1

Intermediate B (4.7 g, 10 mmol), [1,1'-biphenyl]-4-ylboronic acid (2.4 g, 12 mmol), K$_2$CO$_3$ (2.8 g, 20 mmol), and Pd(PPh$_3$)$_4$ (0.41 g, 0.35 mmol) were put into a Schlenk tube, dried under vacuum for 2 hours, and dissolved in 1,4-dioxane (100 mL). N$_2$-purged anhydrous EtOH (20 mL) was added and the mixture was stirred at 140° C. for 48 hours under nitrogen. The resultant was cooled at room temperature, washed with excess DCM and distilled water after a solvent is removed under reduced pressure, and an organic layer is separated. The separated organic layer was dried with MgSO₄ and purified by column chromatography (DCM/EtOH, 99:1, v/v) to obtain 5-(2-([1,1'-biphenyl]-4-yl)-6-(phenanthren-9-yl)pyrimidin-4-yl)-1,10-phenanthroline (1-1) 2.6 g (4.4 mmol, yield 44%). The measured values of NMR data of Compound 1-1 are as follows. ¹NMR (d⁶-DMSO, 500 MHz): δ 9.08 (1H), 8.84-8.80 (3H), 8.50-8.46 (2H), 8.23 (1H), 8.17 (1H), 8.05 (1H), 7.96-7.90 (3H), 7.77-7.62 (9H), 7.49-7.41 (3H), 7.25 (2H) ppm.

Synthesis of Compound 1-4

Compound 1-4 according to an embodiment may be synthesized by, for example, Reaction Formula 2 below.

Synthesis of Intermediate C

Cyanuric chloride (1.8 g, 10 mmol), phenanthren-9-ylboronic acid (2.4 g, 11 mmol), K₂CO₃ (2.8 g, 20 mmol), and Pd(PPh₃)₄ (0.41 g, 0.35 mmol) were put into a Schlenk tube, dried under vacuum for 2 hours, and dissolved in THE (100 mL). N₂-purged anhydrous EtOH (20 mL) was added and the mixture was stirred at 80° C. for 2 hours under nitrogen. The resultant was cooled at room temperature, washed with excess DCM and distilled water after a solvent is removed under reduced pressure, and an organic layer is separated. The separated organic layer was dried with MgSO₄ and purified by column chromatography (dichloromethane/hexane, 3:1, v/v) to obtain 2,4-dichloro-6-(phenanthren-9-yl)-1,3,5-triazine (C) to obtain 2.9 g (8.9 mmol, yield 89%).

[Reaction Formula 2]

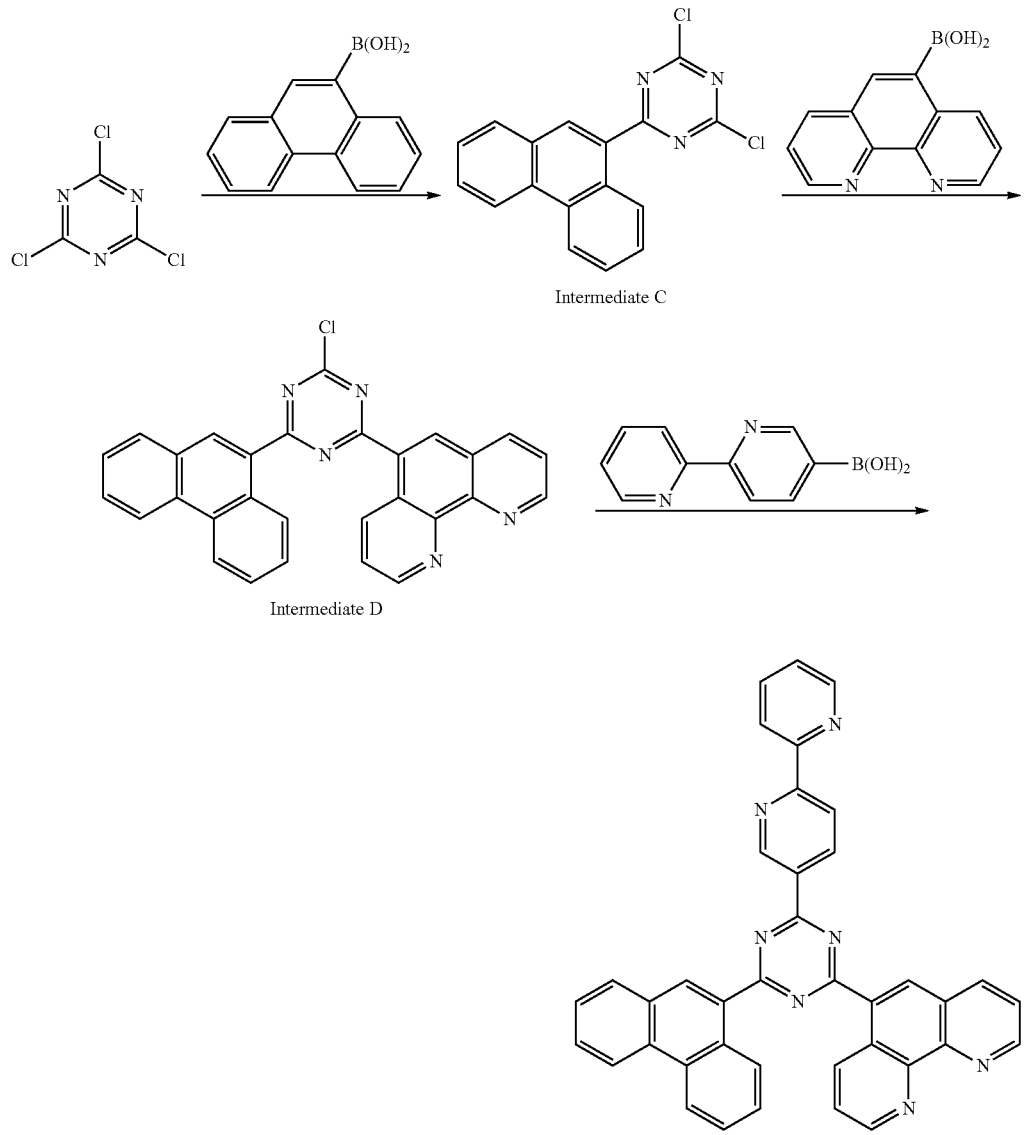

Synthesis of Intermediate D

Intermediate C (3.3 g, 10 mmol), (1,10-phenanthrolin-5-yl)boronic acid (2.6 g, 12 mmol), $K_2CO_3$ (2.8 g, 20 mmol), and $Pd(PPh_3)_4$ (0.41 g, 0.35 mmol) were put into a Schlenk tube, dried under vacuum for 2 hours, and dissolved in DMF (100 mL). $N_2$-purged anhydrous EtOH (20 mL) was added and the mixture was stirred at 100° C. for 48 hours under nitrogen. The resultant was cooled at room temperature, washed with excess DCM and distilled water after a solvent is removed under reduced pressure, and an organic layer is separated. The separated organic layer was dried with $MgSO_4$ and purified by column chromatography (DCM) to obtain 5-(4-chloro-6-(phenanthren-9-yl)-1,3,5-triazin-2-yl)-1,10-phenanthroline (D) 3.4 g (7.2 mmol, yield 72%).

Synthesis of Compound 1-4

Intermediate D (4.7 g, 10 mmol), [2,2'-bipyridin]-5-ylboronic acid (2.4 g, 12 mmol), $K_2CO_3$ (2.8 g, 20 mmol), and $Pd(PPh_3)_4$ (0.41 g, 0.35 mmol) were put into a Schlenk tube, dried under vacuum for 2 hours, and dissolved in 1,4-dioxane (100 mL). $N_2$-purged anhydrous EtOH (20 mL) was added and the mixture was stirred at 140° C. for 48 hours under nitrogen. The resultant was cooled at room temperature, washed with excess DCM and distilled water after a solvent is removed under reduced pressure, and an organic layer is separated. The separated organic layer was dried with $MgSO_4$ and purified by column chromatography (DCM/EtOH, 98:2, v/v) to obtain 5-(4-([2,2'-bipyridin]-5-yl)-6-(phenanthren-9-yl)-1,3,5-triazin-2-yl)-1,10-phenanthroline (1-4) 3.2 g (5.4 mmol, yield 54%). The measured values of NMR data of Compound 1-4 are as follows. $^1$NMR ($d^6$-DMSO, 500 MHz): δ 9.18 (1H), 9.08 (1H), 8.97-8.93 (2H), 8.84-8.80 (3H), 8.48-8.46 (3H), 8.17 (1H), 8.05-8.00 (2H), 7.90 (1H), 7.77-7.62 (8H), 7.23 (1H) ppm.

Synthesis of Compound 1-11

Compound 1-11 according to an embodiment may be synthesized by, for example, Reaction Formula 3 below.

[Reaction Formula 3]

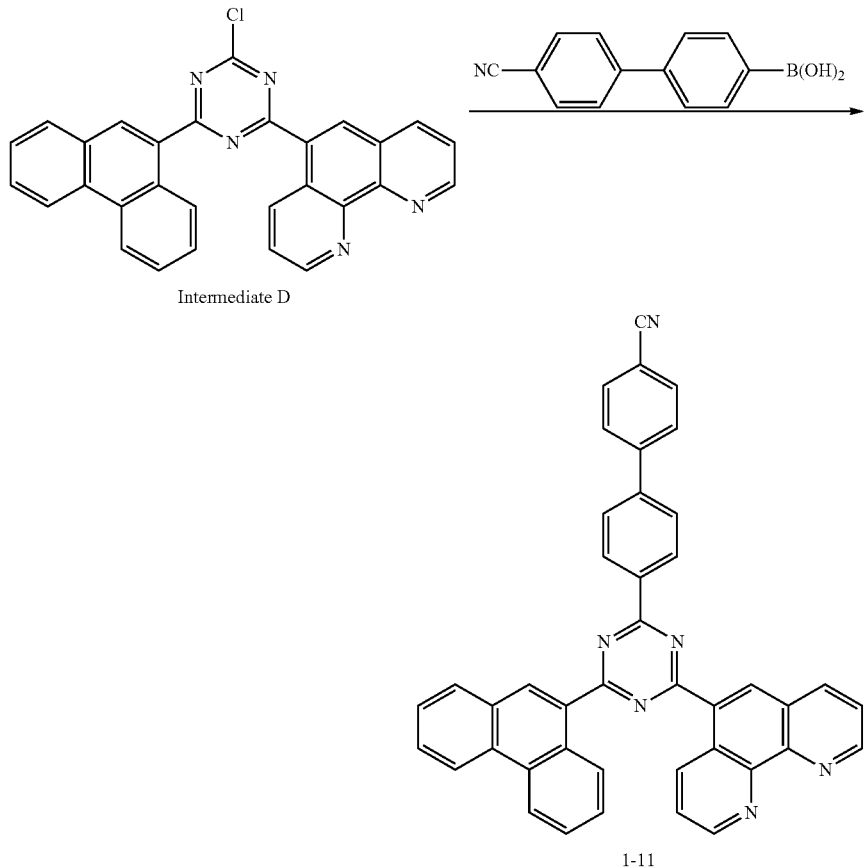

Synthesis of Compound 1-11

D (4.7 g, 10 mmol), (4'-cyano-[1,1'-biphenyl]-4-yl)boronic acid (2.6 g, 12 mmol), $K_2CO_3$ (2.8 g, 20 mmol), and $Pd(PPh_3)_4$ (0.41 g, 0.35 mmol) were put into a Schlenk tube, dried under vacuum for 2 hours, and dissolved in 1,4-dioxane (100 mL). $N_2$-purged anhydrous EtOH (20 mL) was added and the mixture was stirred at 140° C. for 48 hours under nitrogen. The resultant was cooled at room temperature, washed with excess DCM and distilled water after a solvent is removed under reduced pressure, and an organic layer is separated. The separated organic layer was dried with $MgSO_4$ and purified by column chromatography (chloroform:EtOH, 98:2, v/v) to obtain 4'-(4-(phenanthren-9-yl)-

6-(1,10-phenanthrolin-5-yl)-1,3,5-triazin-2-yl)-[1,1'-biphenyl]-4-carbonitrile (1-11) 4.0 g (6.5 mmol, yield 65%). The measured values of NMR data of Compound 1-11 are as follows. ¹NMR (d⁶-DMSO, 500 MHz): δ 9.12 (1H), 8.92-8.81 (3H), 8.55-8.49 (2H), 8.17 (1H), 8.10 (1H), 7.91-7.84 (7H), 7.74-7.59 (7H), 7.33 (2H) ppm.

Synthesis of Compound 1-14

Compound 1-14 according to an embodiment may be synthesized by, for example, Reaction Formula 4 below.

[Reaction Formula 4]

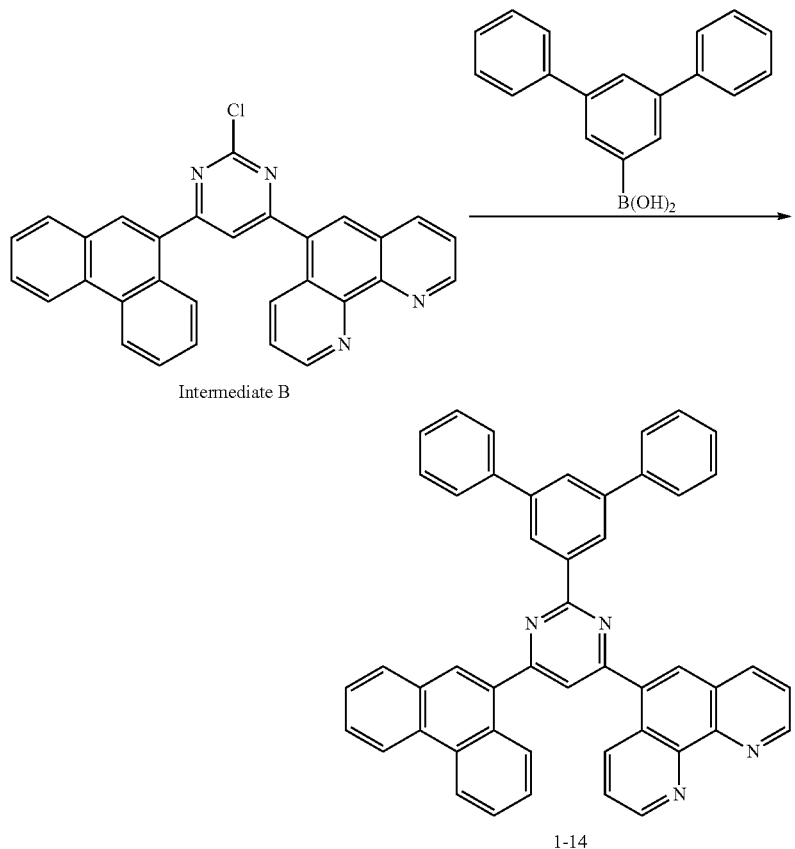

Synthesis of Compound 1-14

B (4.7 g, 10 mmol), [1,1': 3',1''-terphenyl]-5'-ylboronic acid (3.3 g, 12 mmol), K₂CO₃ (2.8 g, 20 mmol), and Pd(PPh₃)₄ (0.41 g, 0.35 mmol) were put into a Schlenk tube, dried under vacuum for 2 hours, and dissolved in 1,4-dioxane (100 mL). N₂-purged anhydrous EtOH (20 mL) was added and the mixture was stirred at 140° C. for 48 hours under nitrogen. The resultant was cooled at room temperature, washed with excess DCM and distilled water after a solvent is removed under reduced pressure, and an organic layer is separated. The separated organic layer was dried with MgSO₄ and purified by column chromatography (chloroform) to obtain 5-(2-([1,1': 3',1''-terphenyl]-5'-yl)-6-(phenanthren-9-yl)pyrimidin-4-yl)-1,10-phenanthroline (1-14) 3.9 g (5.9 mmol, yield 59%). The measured values of NMR data of Compound 1-14 are as follows. ¹NMR (d⁶-DMSO, 500 MHz): δ 9.17 (1H), 8.98-8.86 (3H), 8.52-8.46 (2H), 8.31 (1H), 8.15 (1H), 8.04 (4H), 7.92 (1H), 7.78-7.68 (7H), 7.64-7.62 (4H), 7.50-7.40 (6H) ppm.

2. Manufacture and Evaluation of Organic Electroluminescence Devices Including Compounds of Embodiments (Manufacture of Organic Electroluminescence Devices)

Organic electroluminescence devices of an embodiment including a compound of an embodiment in an electron transport region were manufactured by the following process. The organic electroluminescence devices of Examples 1 to 4 were manufactured using Compounds 1-1, 1-2, 1-11, and 1-14 described above as electron transport layer materials. Compounds used for the manufacture of organic electroluminescence devices of Comparative Examples and Examples are shown below.

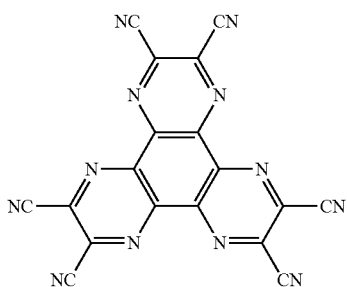

[HAT-CN]

[HT1]
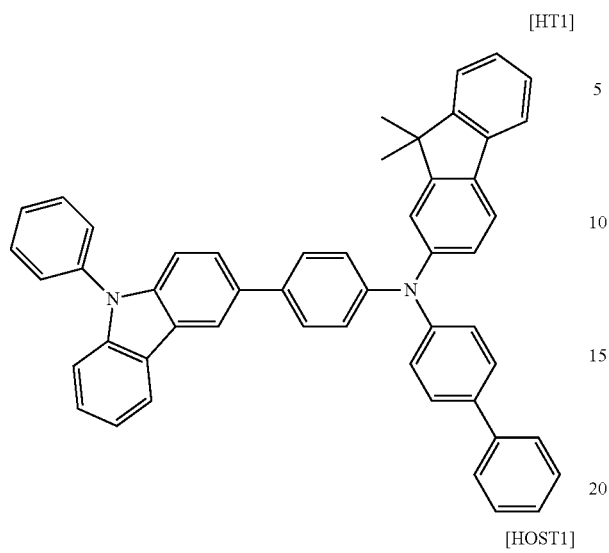
[TPBi]
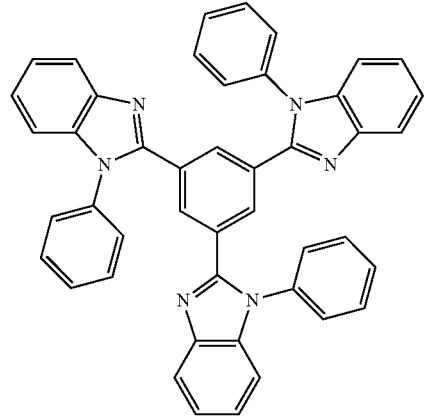
[HOST1]
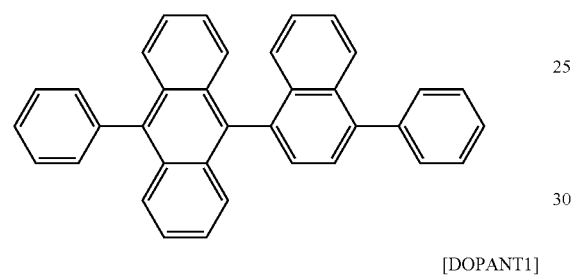
[DOPANT1]
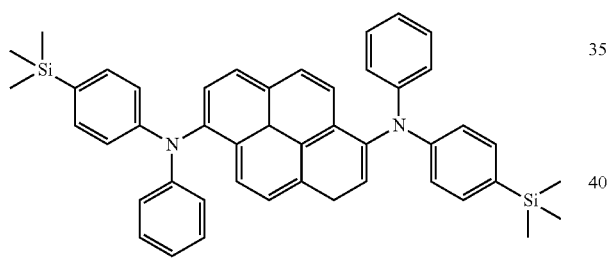
ET1
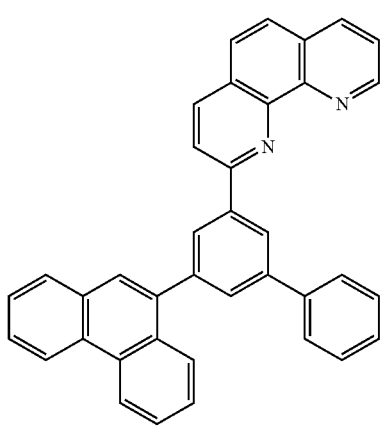
[T2T]
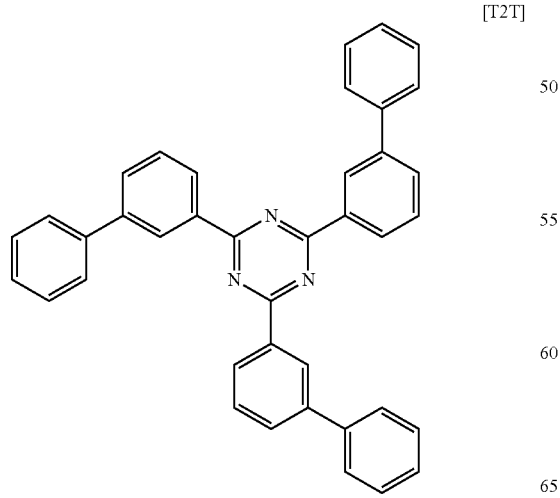
ET2
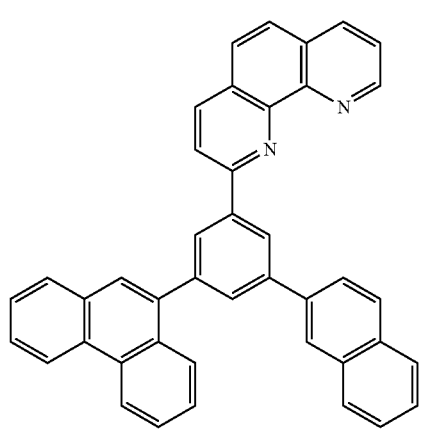

ET3

ET4

1-1

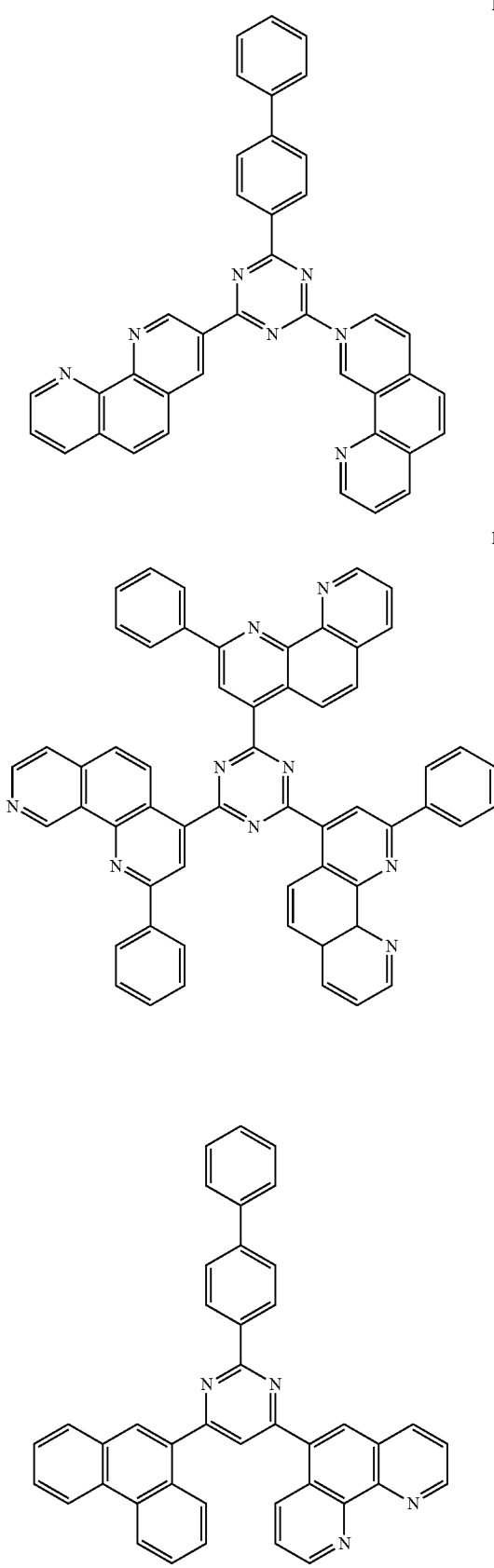

1-4

1-11

1-14

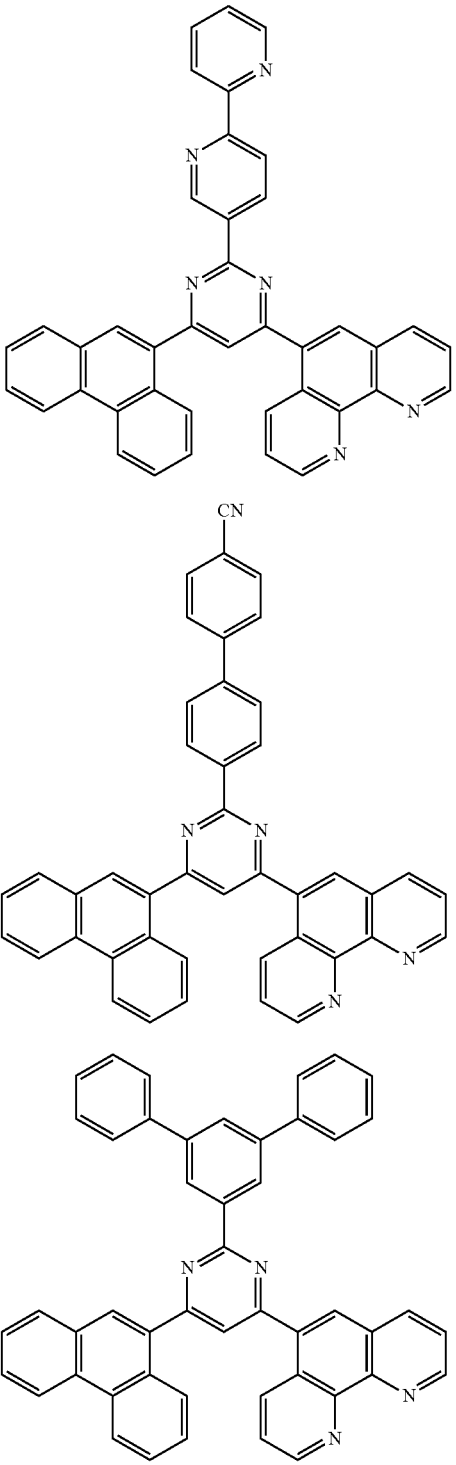

An organic electroluminescence device of Comparative Example 1 was manufactured by the following method. An ITO glass substrate was cut to a size of about 50 mm×50 mm×0.5 mm, subjected to ultrasonic cleaning using isopropyl alcohol and pure water for 10 minutes respectively and ultraviolet irradiation for about 10 minutes, and exposed to ozone for cleaning to form the glass substrate in a vacuum deposition apparatus. HAT-CN was vacuum-deposited to a thickness of about 100 Å to form a hole injection layer, and a first hole transport layer material, HT1 was vacuum-deposited. For an emission layer, HOST1:DOPANT1 was deposited at a wt % ratio of 97:3 to form a thickness of about 300 Å. For a hole blocking layer on the emission layer, T2T was vacuum-deposited to a thickness of 100 Å. For the electron transport layer, TPBi and LiQ (Lithium Quinolate) were vacuum-deposited at a wt % ratio of 1:1 to a thickness of 300 Å. LiF and Al were deposited to a thickness of 8 Å and a thickness of 1000 Å, respectively as an electron injection layer and a cathode.

Organic electroluminescence devices of Comparative Examples 2 to 5 were manufactured in a same manner as used for the manufacture of an organic electroluminescent device of Comparative Example 1, except that ET1 to ET4 were used as electron transport layer materials, respectively.

Organic electroluminescence devices of Examples 1 to 4 were manufactured in a same manner as used for the manufacture of an organic electroluminescent device of Comparative Example 1, except that Compounds 1-1, 1-2, 1-11, and 1-14 were used as electron transport layer materials, respectively.

(Evaluation of Organic Electroluminescence Device Characteristics)

Table 1 shows the evaluation results on organic electroluminescence devices of Examples 1 to 4, and Comparative Examples 1 to 5. Table 1 compares and shows driving voltage, light emission efficiency, and device life of the manufactured organic electroluminescence devices. In the characteristic evaluation results of Examples and Comparative Examples shown in Table 1, the light emission efficiency indicates an efficiency value at the current density corresponding to luminance 1000 nit, and the device life T95 indicates the time taken to reduce 500 of the initial luminance.

TABLE 1

| | Type | | | |
|---|---|---|---|---|
| | Electron Transport Layer | Efficiency EQE (%) | Driving Voltage (V) | Device Life T95 (h) |
| Comparative Example 1 | TPBi | 4.2 | 5.1 | 15 |
| Comparative Example 2 | ET1 | 6.1 | 4.5 | 42 |
| Comparative Example 3 | ET2 | 5.9 | 4.8 | 30 |
| Comparative Example 4 | ET3 | 6.3 | 4.3 | 47 |
| Comparative Example 5 | ET4 | 4.9 | 5.0 | 19 |
| Example 1 | Compound 1-1 | 8.7 | 3.9 | 75 |
| Example 2 | Compound 1-2 | 9.2 | 3.5 | 89 |
| Example 3 | Compound 1-11 | 8.4 | 3.7 | 72 |
| Example 4 | Compound 1-14 | 8.0 | 3.8 | 64 |

Table 1 shows that Examples of organic electroluminescence devices including the compound of an embodiment as an electron transport layer material exhibit excellent device characteristics. For example, it is seen that the organic electroluminescence devices of Examples 1 to 4 exhibit low driving voltage, high efficiency, and long life characteristics compared to the organic electroluminescence devices of Comparative Examples 1 to 5.

In TPBi included in the electron transport layer of Comparative Example 1, the central ring is a benzene ring, and phenanthrene and phenanthroline are not bonded to a benzene ring group. Accordingly, it is seen that Comparative Example 1 shows the highest driving voltage, low efficiency, and low life among Comparative Examples.

ET1 and ET2 included in the electron transport layer of Comparative Examples 2 and 3 include phenanthrene and phenanthroline, but are different from compounds included in the electron transport layer of Examples 1 to 4, in that a central ring bonded to phenanthrene and phenanthroline is a benzene ring. The compounds included in the electron transport layer of Examples 1 to 4 are triazine in which a nitrogen atom is contained in the central ring. As a result, it is seen that Examples 1 to 4 exhibit lower driving voltage, high efficiency, and long life characteristics. This is because Examples 1 to 4, unlike Comparative Examples 2 and 3, include compounds containing nitrogen atoms in the central ring in the electron transport layer to induce electron deficiency in the ring, thereby having improved electron transport ability.

ET3 and ET4 included in the electron transport layer of Comparative Examples 4 and 5 include triazine as a central ring, but are different from compounds included in the electron transport layer of Examples 1 to 4, in that at least two phenanthroline groups are bonded to the central ring. The compounds included in the electron transport layer of Examples 1 to 4 are bonded to one phenanthroline group in the central ring. As a result, it is seen that Examples 1 to 4 exhibit lower driving voltage, high efficiency, and long life characteristics. This is because Examples 1 to 4, unlike Comparative Examples 4 and 5, include compounds containing fewer phenanthroline groups and containing phenanthrene in the electron transport layer to increase the electron transport rate, and thus the increased electron transport rate contributes to low driving voltage, high efficiency and long life characteristics.

The compound of an embodiment is included in the electron transport region, and may thus contribute to increasing the electron transport rate, and the compound of an embodiment exhibiting the increased electron transport rate is included in the organic electroluminescence device of an embodiment, and may thus contribute to lowering driving voltage, and improving light emission efficiency and lifespan. Accordingly, the organic electroluminescent device of an embodiment may have low driving voltage, high efficiency, and long life characteristics.

An organic electroluminescence device of an embodiment includes a compound of an embodiment in an electron transport region, and may thus exhibit low driving voltage, high efficiency, and long life characteristics.

A compound of an embodiment may enhance a driving voltage, light emission efficiency, and device life of an organic electroluminescence device.

Although the inventive concept has been described with reference to an embodiment of the inventive concept, it will be understood that the inventive concept should not be limited to these embodiments but various changes and modifications can be made by those skilled in the art without departing from the spirit and scope of the inventive concept.

Accordingly, the technical scope of the inventive concept is not intended to be limited to the contents set forth in the detailed description of the specification, but is intended to be defined by the appended claims.

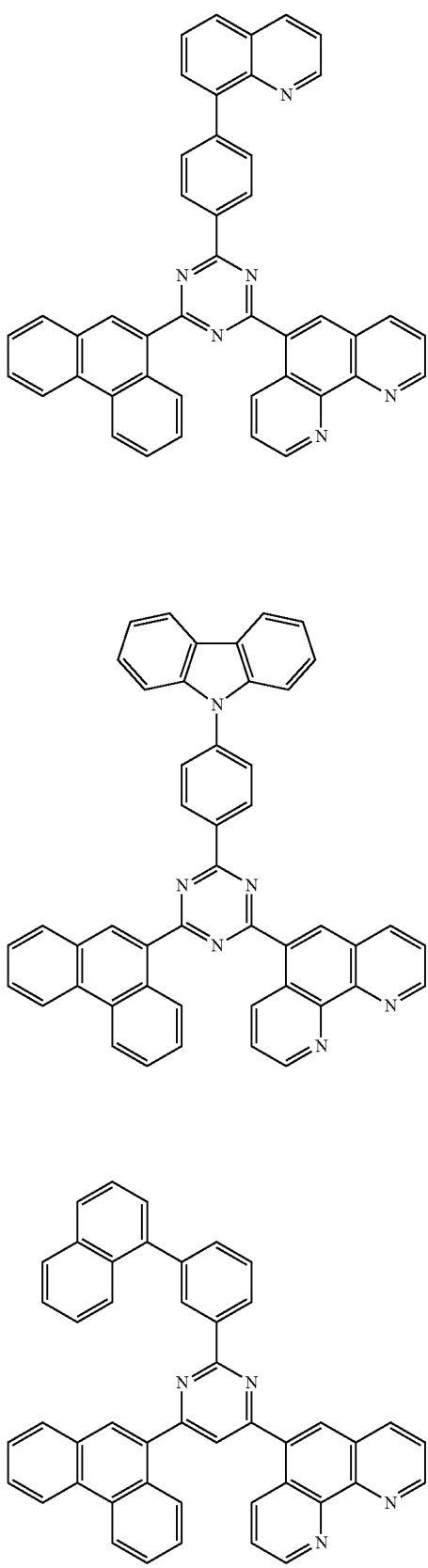
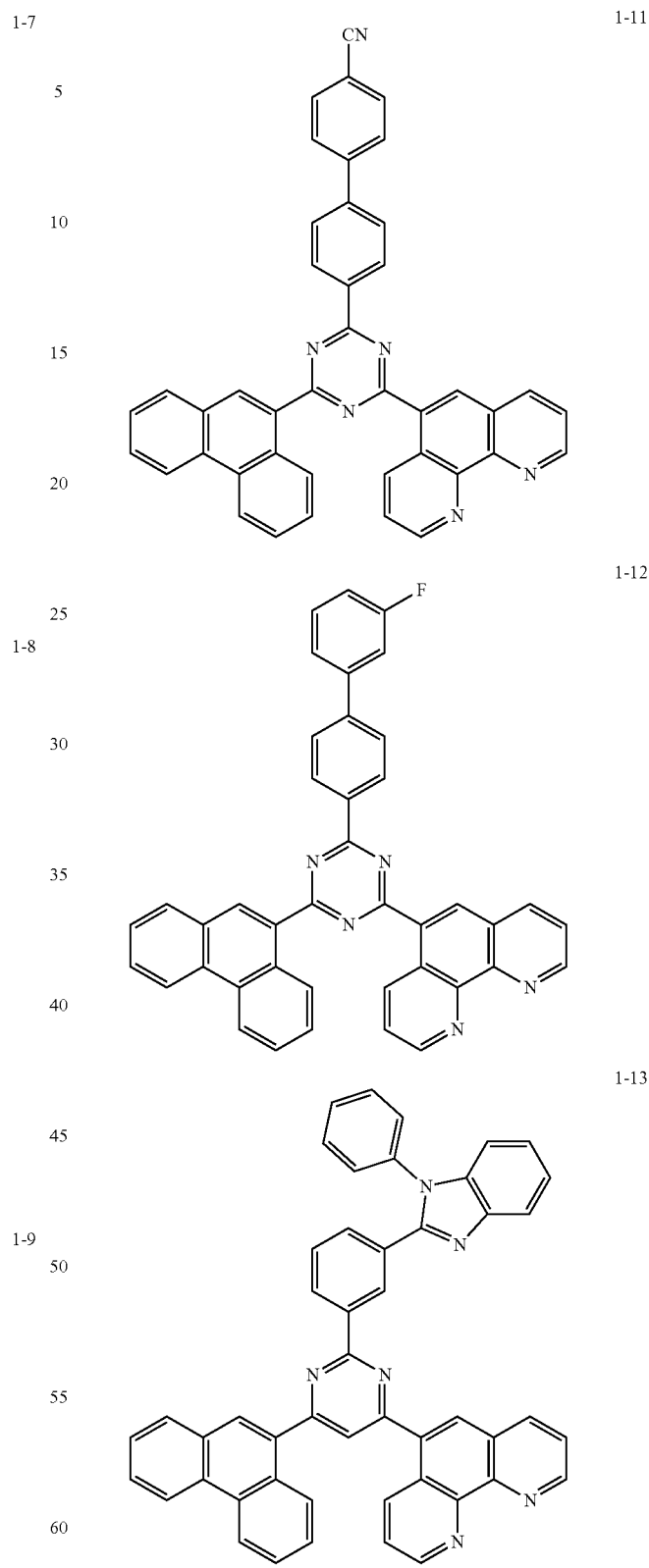

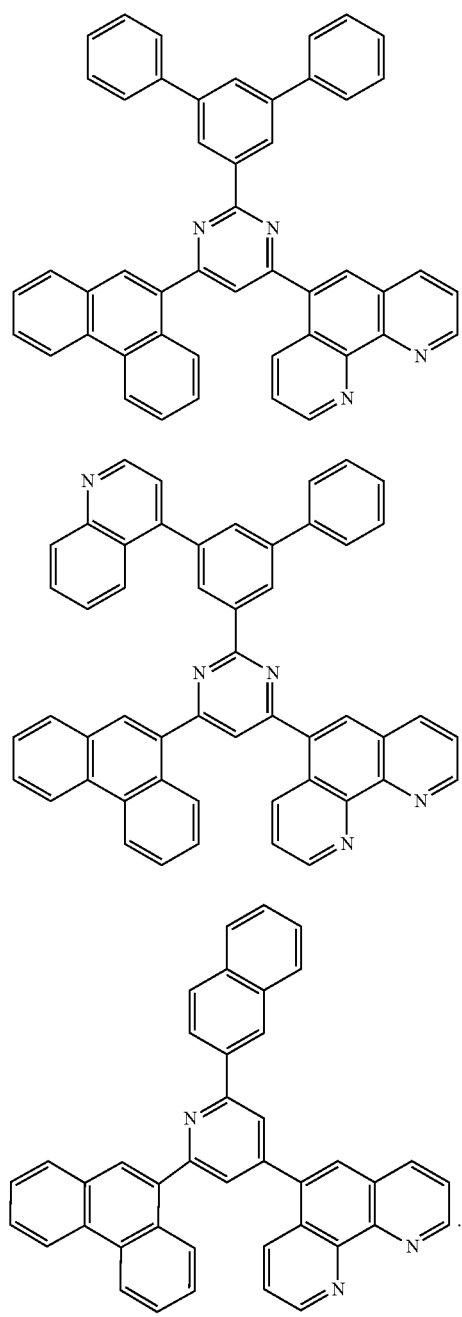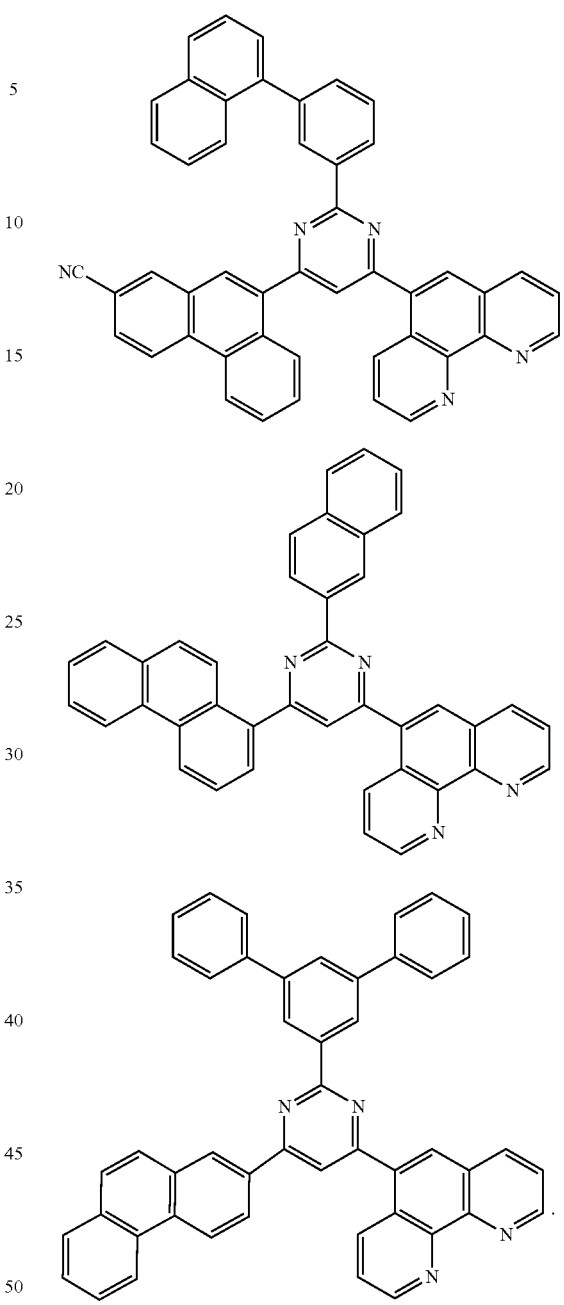

What is claimed is:

1. An organic electroluminescence device comprising:
a first electrode;
a second electrode disposed on the first electrode; and
a plurality of functional layers disposed between the first electrode and the second electrode,
wherein at least one of the plurality of functional layers comprises a compound represented by Formula 1-4 or Formula 1-5:

[Formula 1-4]

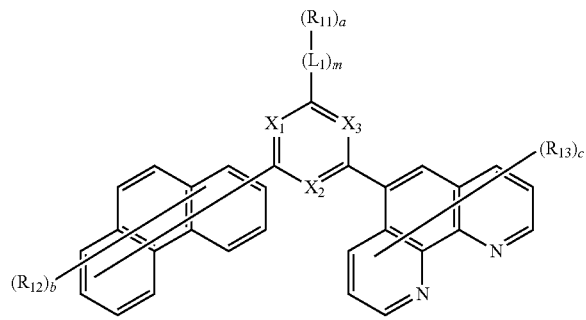

[Formula 1-5]

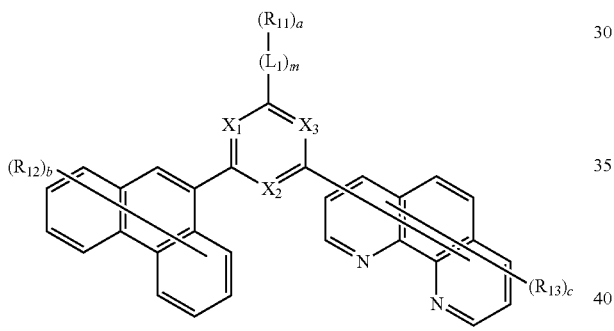

wherein in Formula 1-4 or Formula 1-5,
at least one of $X_1$ to $X_3$ is N, and the remainder are each $CR_1$,
$R_{11}$ is a substituted or unsubstituted aryl group having 6 to 60 ring-forming carbon atoms, or a substituted or unsubstituted heteroaryl group having 1 to 60 ring-forming carbon atoms,
$R_{12}$, $R_{13}$, and $R_1$ are each independently a hydrogen atom, a deuterium atom, a halogen atom, a cyano group, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted aryl group having 6 to 60 ring-forming carbon atoms, or a substituted or unsubstituted heteroaryl group having 1 to 60 ring-forming carbon atoms,
$L_1$ is substituted or unsubstituted phenylene group, a substituted or unsubstituted divalent biphenyl group, a substituted or unsubstituted pyridylene group, or a substituted or unsubstituted divalent bipyridyl group,
a is an integer from 1 to 4,
b is an integer from 0 to 9,
c is an integer from 0 to 7,
m is an integer from 0 to 3, when m is 0 and a is 1, then $R_{11}$ is substituted or unsubstituted naphthyl group, and when $L_1$ is unsubstituted phenylene group, m is 1, and a is 1, then $R_{11}$ is neither an unsubstituted phenyl group nor an unsubstituted pyridine group.

2. The organic electroluminescence device of claim 1, wherein the compound represented by Formula 1-4 or Formula 1-5 is represented by one of Formulas 1A to 1C:

[Formula 1A]

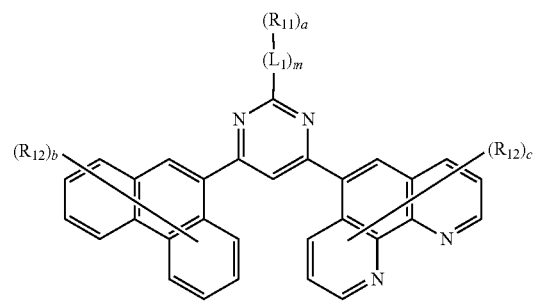

[Formula 1B]

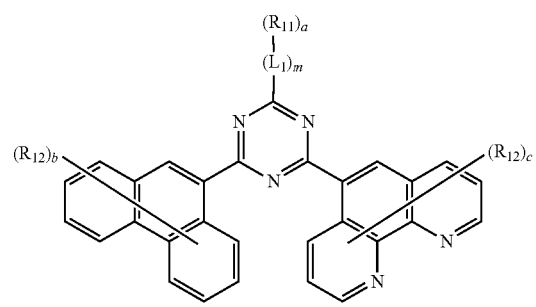

[Formula 1C]

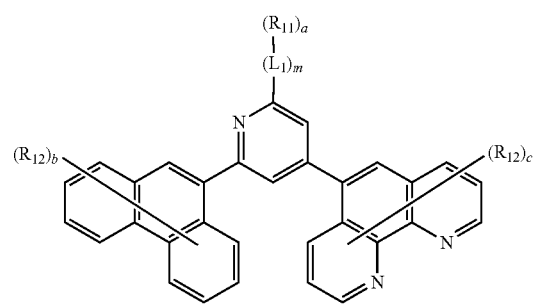

wherein in Formulas 1A to 1C,
$R_{11}$, $R_{12}$, $R_{13}$, $L_1$, a to c, and m are the same as defined in Formula 1.

3. The organic electroluminescence device of claim 1, wherein
$L_1$ does not contain a divalent phenanthroline group, and
$R_1$ does not contain a phenanthroline group.

4. The organic electroluminescence device of claim 1, wherein R11 is represented by one of Formulas R1-1 to R1-9:

R1-1

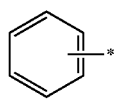

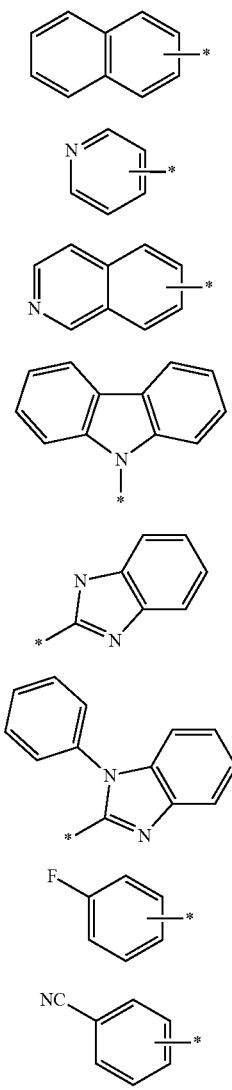

wherein in Formulas R1-1 to R1-9,
* indicates a binding site to a neighboring atom.

5. The organic electroluminescence device of claim 1, wherein the plurality of functional layers comprise:
an emission layer;
a hole transport region disposed between the first electrode and the emission layer; and
an electron transport region disposed between the emission layer and the second electrode, wherein
the electron transport region comprises the compound represented by Formula 1-4 or Formula 1-5.

6. The organic electroluminescence device of claim 5, wherein the electron transport region comprises:
an electron transport layer;
a hole blocking layer disposed between the emission layer and the electron transport layer; and
an electron injection layer disposed between the second electrode and the electron transport layer, and
wherein at least one selected from the electron transport layer, the hole blocking layer, and the electron injection layer comprises the compound represented by Formula 1-4 or Formula 1-5.

7. The organic electroluminescence device of claim 1, wherein the plurality of functional layers comprise:
a plurality of light emitting units; and
at least one charge generating layer disposed between adjacent ones of the plurality of light emitting units, and
at least one selected from the plurality of light emitting units and the at least one charge generating layer comprises the compound represented by Formula 1-4 or Formula 1-5.

8. The organic electroluminescence device of claim 7, wherein
each of the plurality of light emitting units comprises a hole transport region, an emission layer, and an electron transport region which are sequentially stacked, and
at least one selected from the plurality of electron transport regions and charge generating layer comprises the compound represented by Formula 1-4 or Formula 1-5.

9. The organic electroluminescence device of claim 1, wherein the compound represented by Formula 1-4 or Formula 1-5 is one of Compounds 1-4 to 1-9, 1-11 to 1-15, 1-17, 1-19, 1-24, and 1-26:

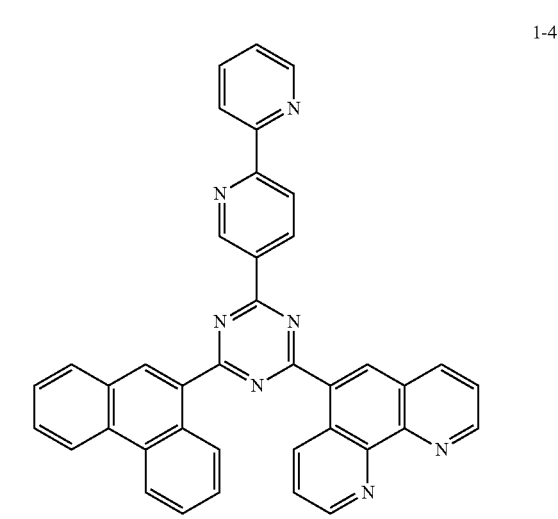

1-4

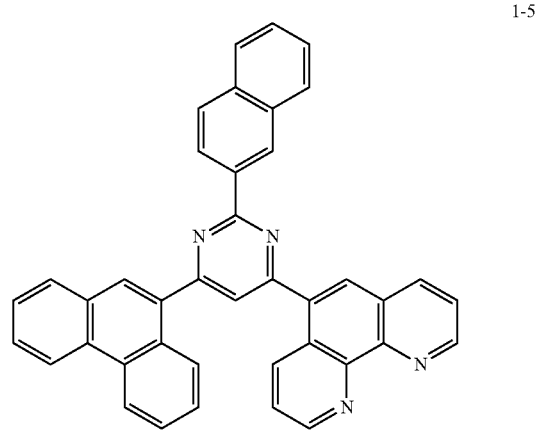

1-5

1-6
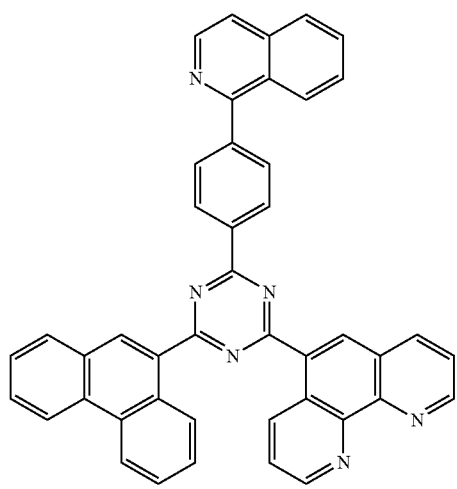
1-7
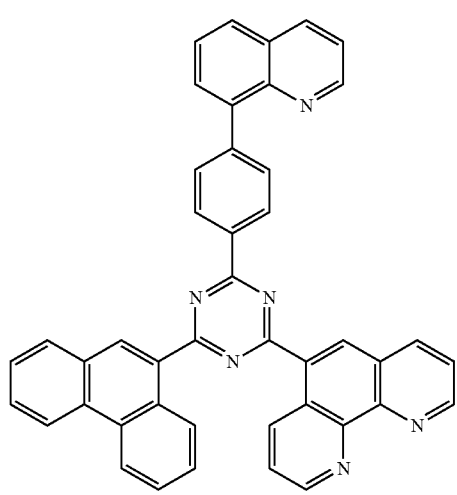
1-8
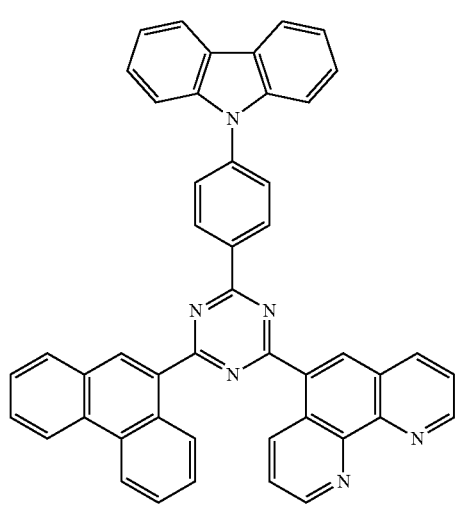
1-9
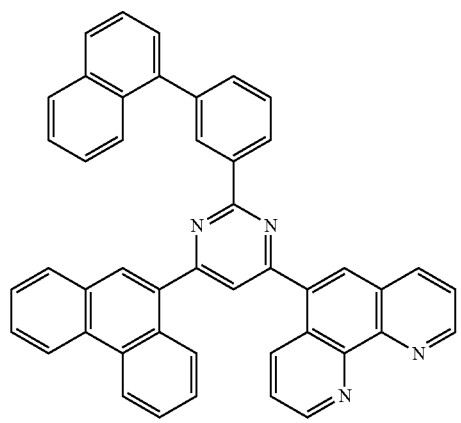
1-11
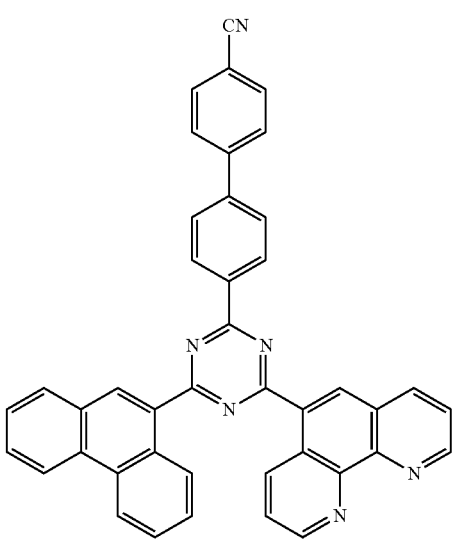
1-12
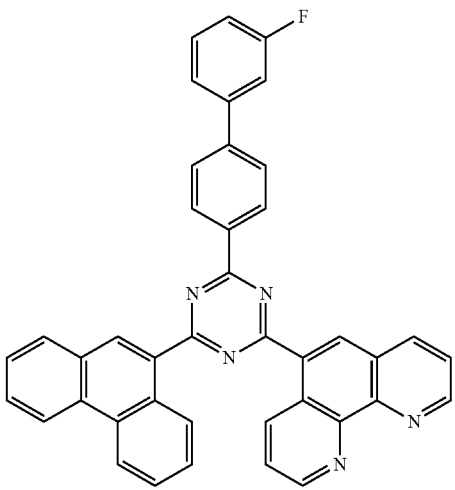

1-13
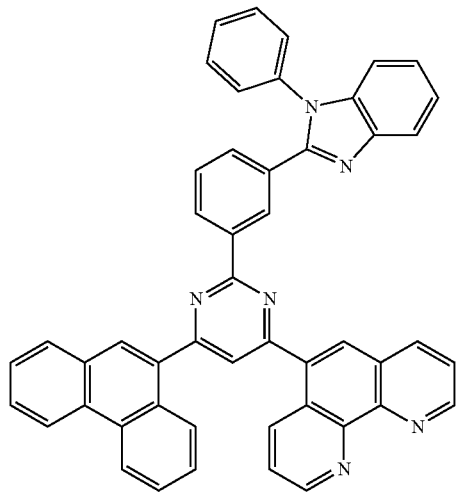
1-14
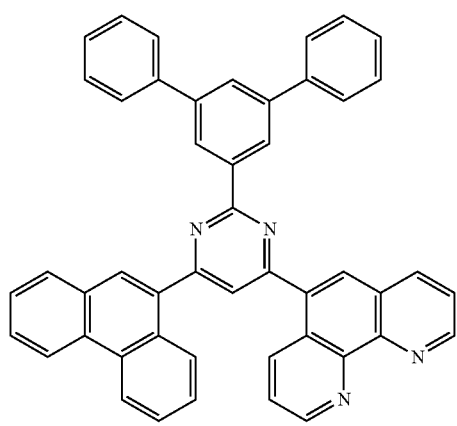
1-15
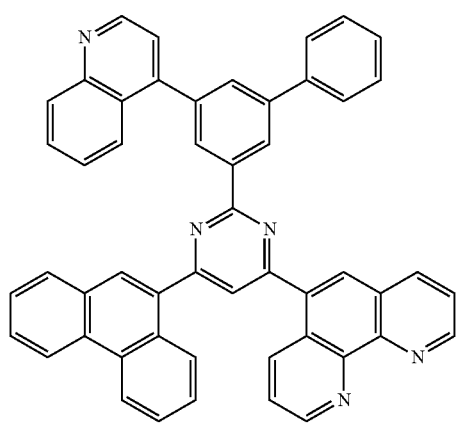
1-17
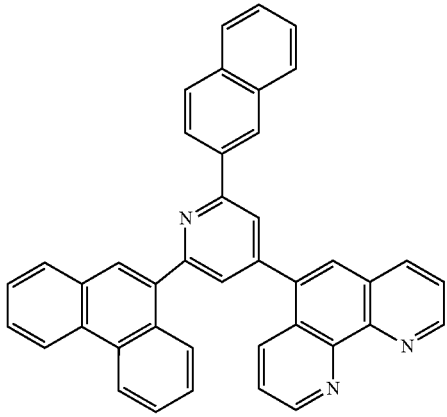
1-19
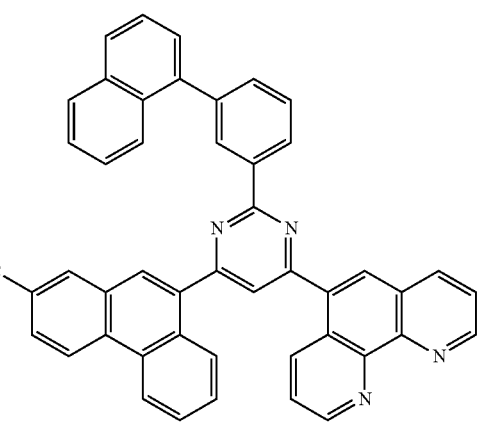
1-24
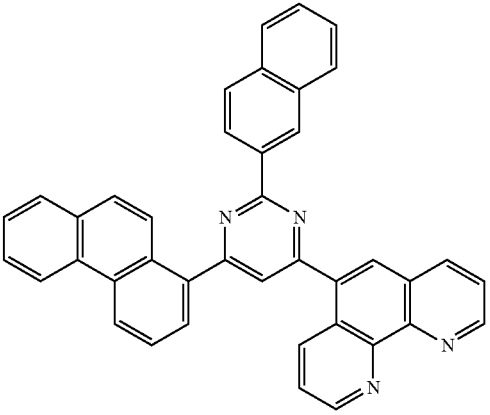

-continued

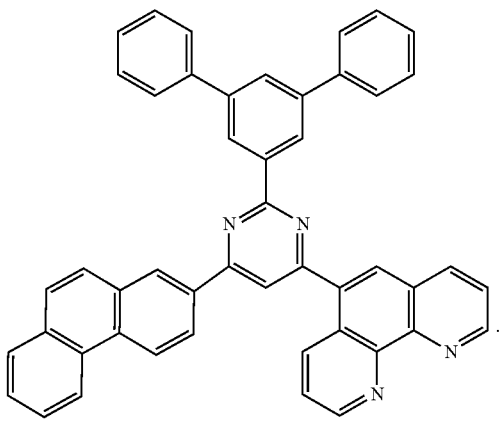

1-26

10. A compound represented by Formula 1-4 or Formula 1-5:

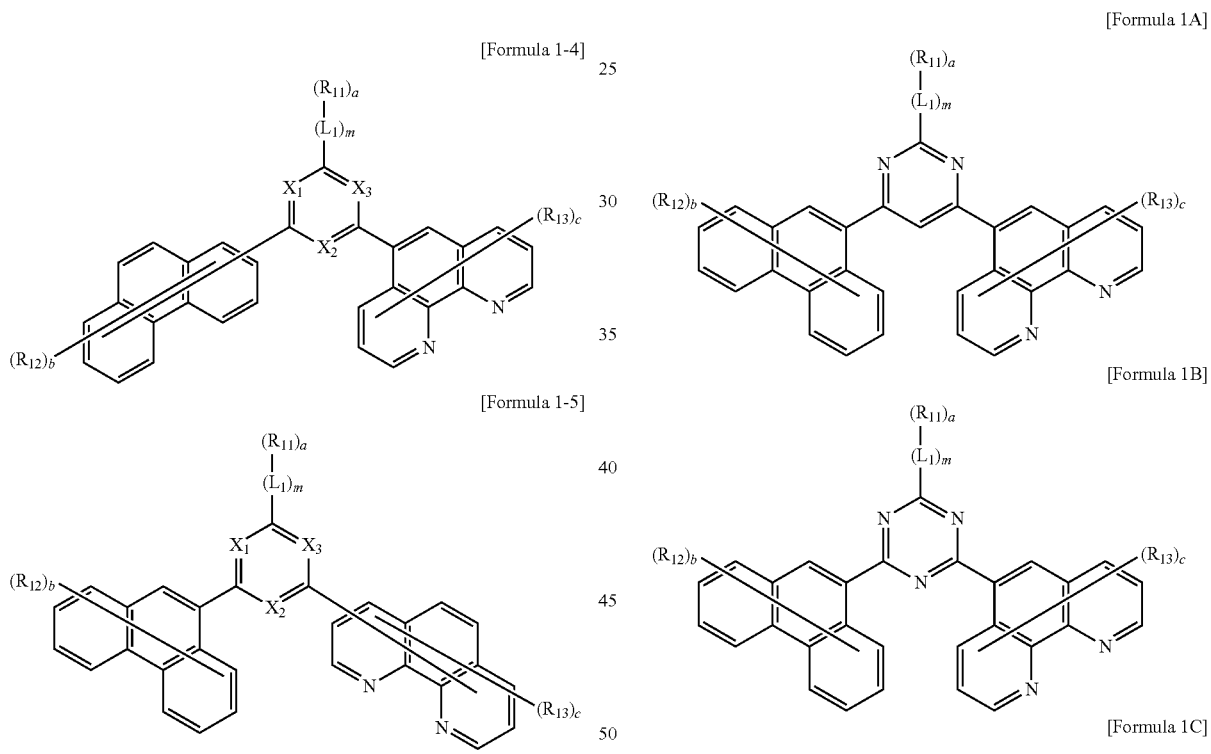

wherein in Formula 1-4 and Formula 1-5, at least one of $X_1$ to $X_3$ is N and the remainder are each $CR_1$, $R_{11}$ is a substituted or unsubstituted aryl group having 6 to 60 ring-forming carbon atoms, or a substituted or unsubstituted heteroaryl group having 1 to 60 ring-forming carbon atoms, $R_{12}$, $R_{13}$ and $R_1$ are each independently a hydrogen atom, a deuterium atom, a halogen atom, a cyano group, a substituted or unsubstituted alkyl group having 1 to 60 carbon atoms, a substituted or unsubstituted alkenyl group having 2 to 60 carbon atoms, a substituted or unsubstituted alkynyl group having 2 to 60 carbon atoms, a substituted or unsubstituted aryl group having 6 to 60 ring-forming carbon atoms, or a substituted or unsubstituted heteroaryl group having 1 to 60 ring-forming carbon atoms, $L_1$ is a substituted or unsubstituted phenylene group, a substituted or unsubstituted divalent biphenyl group, a substituted or unsubstituted pyridylene group, or a substituted or unsubstituted divalent bipyridyl group, a is an integer from 1 to 4, b is an integer from 0 to 9, c is an integer from 0 to 7, m is an integer from 0 to 3, when m is 0 and a is 1, then Ru is substituted or unsubstituted naphthyl group, and when $L_1$ is unsubstituted phenylene group, m is 1, and a is 1, then $R_{11}$ is neither an unsubstituted phenyl group nor an unsubstituted pyridine group.

11. The compound of claim 10, wherein the compound represented by Formula 1-4 or Formula 1-5 is represented by one of Formulas 1A to 1C:

wherein in Formulas 1A to 1C, $R_{11}$, $R_{12}$, $R_{13}$, $L_1$, a to c, and m are the same as defined in Formula 1-4 and Formula 1-5.

12. The compound of claim 10, wherein $L_1$ does not contain a divalent phenanthroline group, and $R_1$ does not contain a phenanthroline group.

13. The compound of claim 10, wherein R11 is represented by one of Formulas R1-1 to R1-9:

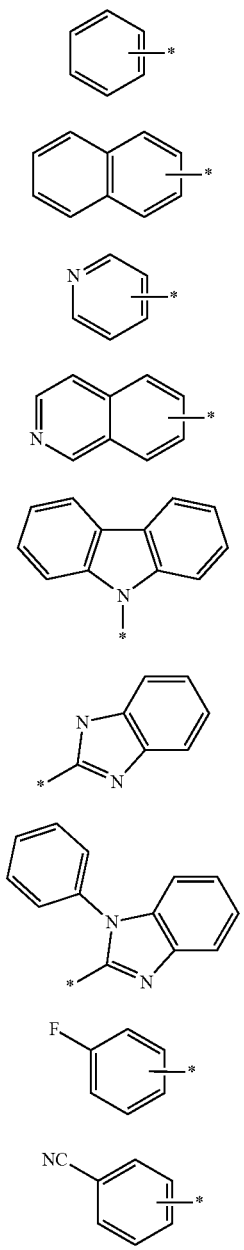

R1-1

R1-2

R1-3

R1-4

R1-5

R1-6

R1-7

R1-8

R1-9 wherein in Formulas R1-1 to R1-9,

\* indicates a binding site to a neighboring atom.

14. The compound of claim 10, wherein the compound represented by Formula 1-4 or Formula 1-5 is one of Compounds 1-4 to 1-9, 1-11 to 1-15, 1-17, 1-19, 1-24, and 1-26:

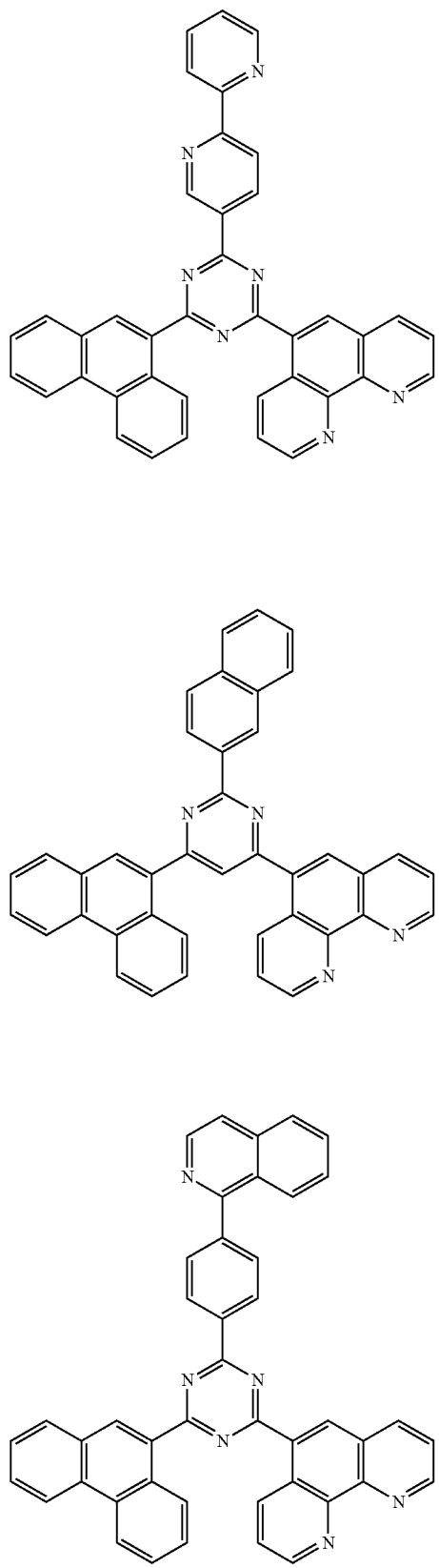

1-4

1-5

1-6